(12) United States Patent
Futami et al.

(10) Patent No.: US 8,697,446 B2
(45) Date of Patent: Apr. 15, 2014

(54) CELL FUSION CHAMBER, CELL FUSION DEVICE, AND METHOD FOR CELL FUSION USING THE SAME

(75) Inventors: Toru Futami, Yokohama (JP); Takahiro Maruyama, Ebina (JP); Atsushi Morimoto, Kawasaki (JP)

(73) Assignee: Tosoh Corporation, Shunan-shi (JP)

( * ) Notice: Subject to any disclaimer, the term of this patent is extended or adjusted under 35 U.S.C. 154(b) by 0 days.

(21) Appl. No.: 13/619,193

(22) Filed: Sep. 14, 2012

(65) Prior Publication Data
US 2013/0011899 A1 Jan. 10, 2013

Related U.S. Application Data

(62) Division of application No. 11/423,023, filed on Jun. 8, 2006, now abandoned.

(30) Foreign Application Priority Data

Jun. 13, 2005 (JP) ................................. 2005-171915
Apr. 3, 2006 (JP) ................................. 2006-102382

(51) Int. Cl.
*C12N 15/02* (2006.01)
*C12N 13/00* (2006.01)
(52) U.S. Cl.
USPC ..... 435/450; 435/440; 435/173.1; 435/287.2; 435/285.2; 435/446; 435/173.4; 435/173.5; 435/449; 435/173.6
(58) Field of Classification Search
USPC ........ 435/450, 440, 173.1, 287.2, 285.2, 446, 435/173.4, 173.5, 449, 173.6
See application file for complete search history.

(56) References Cited

U.S. PATENT DOCUMENTS

| 4,804,450 A | 2/1989 | Mochizuki et al. |
| 5,173,158 A | 12/1992 | Schmukler |
| 5,187,096 A | 2/1993 | Giaever et al. |

(Continued)

FOREIGN PATENT DOCUMENTS

| DE | 285 992 A5 | 1/1991 |
| DE | 103 59 189 A1 | 7/2005 |

(Continued)

OTHER PUBLICATIONS

International Search Report issued Jul. 14, 2009 in PCT/JP09/57611 filed Apr. 15, 2009.

(Continued)

*Primary Examiner* — Nathan Bowers
(74) *Attorney, Agent, or Firm* — Oblon, Spivak, McClelland, Maier & Neustadt, L.L.P.

(57) ABSTRACT

The present invention relates to a cell fusion chamber in which two types of cells having different diameters are fused, the cell fusion chamber including: a cell fusion region in which cell fusion is carried out; a pair of electrodes formed by a conductor and disposed opposite to each other in the cell fusion region; and a partition wall having at least one fine pore; near the fine pore, a cell fusion device including a cell fusion container containing a cell fusion region; a pair of electrodes; a spacer; and an insulator disposed between the spacer and one of the electrodes and having at least one fine pore; and an electronic power supply which applies an alternating voltage and a voltage pulsed direct current to the electrodes, and a cell fusion method using the same.

8 Claims, 20 Drawing Sheets

(56) References Cited

U.S. PATENT DOCUMENTS

| | | | |
|---|---|---|---|
| 5,304,486 | A | 4/1994 | Chang |
| 5,310,674 | A | 5/1994 | Weinreb et al. |
| 5,589,047 | A | 12/1996 | Coster et al. |
| 5,795,457 | A | 8/1998 | Pethig et al. |
| 6,479,644 | B1 | 11/2002 | Bertling |
| 7,572,623 | B2 | 8/2009 | Mangano et al. |
| 2003/0141294 | A1 | 7/2003 | Jaroszeski et al. |
| 2004/0106189 | A1* | 6/2004 | Dodgson et al. ............ 435/285.2 |
| 2005/0048653 | A1 | 3/2005 | Walters et al. |
| 2005/0112544 | A1 | 5/2005 | Xu et al. |
| 2006/0019378 | A1 | 1/2006 | Nagasaki et al. |
| 2006/0246572 | A1* | 11/2006 | Ragsdale et al. ............ 435/285.2 |
| 2006/0281168 | A1 | 12/2006 | Futami et al. |
| 2011/0033910 | A1 | 2/2011 | Yamanaka et al. |

FOREIGN PATENT DOCUMENTS

| | | |
|---|---|---|
| DE | 103 59 190 A1 | 7/2005 |
| JP | 60-251871 | 12/1985 |
| JP | 63-181992 | 7/1988 |
| JP | 1-165366 | 6/1989 |
| JP | 1-215274 | 8/1989 |
| JP | 2-92275 | 4/1990 |
| JP | 4-299972 | 10/1992 |
| JP | 7-4218 | 1/1995 |
| JP | 7-40914 | 5/1995 |
| JP | 2000-515508 | 11/2000 |
| JP | 2001-281250 | 10/2001 |
| JP | 2004-73112 | 3/2004 |
| JP | 3723882 | 9/2005 |
| JP | 2006-6250 | 1/2006 |
| JP | 3799392 | 5/2006 |
| JP | 2007-20444 | 2/2007 |
| JP | 2007-295922 | 11/2007 |
| JP | 200854630 | 3/2008 |
| WO | WO 93/05166 | 3/1993 |
| WO | WO 00/60065 | 10/2000 |
| WO | WO 03/014337 A2 | 2/2003 |

OTHER PUBLICATIONS

Extended European Search Report issued Mar. 17, 2011, in Application No. / Patent No. 09732387.7-1223 / 2270126 PCT/JP2009057611.

Office Action mailed Mar. 14, 2012, in U.S. Appl. No. 12/937,603.

Groebner et al., "Polylysine supports electrofusion," Bioelectrochemistry and Bioenergetics 39, 1996, pp. 181-184.

Mark J. Jaroszeski, et al., "Detection and Quantitation of Cell-Cell Electrofusion Products by Flow Cytometry", Analytical Biochemistry, XP-002347458, vol. 216, 1994, pp. 271-275.

Japanese Office Action issued Oct. 4, 2011 in patent application No. 2006-160744 with partial English translation.

* cited by examiner

CELL FUSION CHAMBER, CELL FUSION DEVICE, AND METHOD FOR CELL FUSION USING THE SAME

CROSS REFERENCE TO RELATED APPLICATIONS

The present application is a divisional of and claims the benefit of priority under 35 U.S.C. §120 from U.S. application Ser. No. 11/423,023, filed Jun. 8, 2006, which claims the benefit of priority under U.S.C. §119 from prior Japanese Patent Application No. 2005-171915, filed on Jun. 13, 2005, and Japanese Patent Application No. 2006-102382, filed on Apr. 3, 2006, the entire contents of each of which is incorporated herein by reference.

BACKGROUND OF THE INVENTION

1. Field of the Invention

The present invention relates to a chamber and a device for effectively performing cell fusion and a method for cell fusion using the same.

2. Description of the Related Art

In the prior art, a chemical fusion method mainly using polyethyleneglycol (PEG) is used as a cell fusion technique for fusing different cells to obtain a hybridoma. However, this method has the following problems to be solved, for example: (i) PEG exhibits a strong toxicity against cells; (ii) a great deal of effort is required in finding the optimal conditions for cell fusion with respect to the polymerization degree or amount of PEG added, or the like; (iii) an advanced technique is required for carrying out cell fusion, and so only a person skilled in a particular technique can use this method; (iv) since contact between two cells accidentally occurs, it is difficult to control cell fusion of two cells, and so the probability of successful cell fusion is extremely low.

In contrast, an electrical cell fusion method has an advantage in that an advanced technique is not required, cell fusion can be easily and effectively carried out, toxicity is almost not exhibited against cells, and cells can be fused with high activity. The electrical cell fusion method was established by Zimmermann in 1981 in Western Germany and the theory thereof is as follows. An alternating voltage is applied to parallel electrodes, and cells are introduced therein, as a result of which the cells are drawn toward the area having higher current density and thus linearly linked together. The state in which cells are linearly linked together is generally referred to as a pearl chain. In this state, a voltage pulsed direct current is applied between electrodes at intervals of a few micro seconds to several tens of micro seconds, as a result of which electrical conductance of the cellular membrane instantly decreases, and thereby cellular membranes constituted by a lipid bilayer are reversibly disrupted and then reconstituted, and thus cell fusion is performed.

As the electrical fusion method, a microelectrode method and a parallel electrode method are mainly used. The microelectrode method is a method in which two cells are fused by picking up the cells by operating a micromanipulator while observing them using a microscope, and then applying a voltage pulsed direct current thereto. This method enables extremely reliable cell fusion. Moreover, an electrode of the micromanipulator has been reported (see, for example, Patent Document 1 (Japanese Examined Patent Application, Second Publication No. H 7-40914)). However, the microelectrode method requires lengthy procedure, the operation of the micromanipulator requires skill, and the method is not practical in view of dealing with a large number of cells. In contrast, the parallel electrode method is a method in which a voltage pulsed direct current is applied to a pearl chain formed by plural cells subjected to dielectrophoresis, and the handling thereof is easy. However, since the plural cells linearly linked together are fused, contact between two cells accidentally occurs, and so there is a problem in that it is difficult to reliably control cell fusion of two cells.

In order to solve the problem of the parallel electrode method, a cell fusion chamber composed of a pair of electrodes formed by a conductor and placed opposite to each other in a cell fusion region and an insulator placed between the pair of electrodes and having a fine pore passing therethrough in the direction of the pair of electrodes has been reported (see, for example, Patent Document 2 (Japanese Examined Patent Application, Second Publication No. H 7-4218)).

FIG. 1 is a schematic diagram showing a cross-sectional view of the above-mentioned cell fusion chamber. In FIG. 1, electrodes (2) formed of a conductor are placed at both sides of a cell fusion region (1) in a cell fusion chamber formed of a resin, for example. To these electrodes, an electronic power supply (4) placed outside is connected through a conductor (3). The electronic power supply (4) is composed of an alternating-current power supply (5) outputting a high-frequency alternating voltage with an electrical field strength of approximately 400 V/cm to 700 V/cm and a frequency of approximately 1 MHz, a direct current pulsed power supply (6) outputting a voltage pulsed direct current with an electrical field strength of approximately 7 kV/cm and a pulse width of 50µ seconds, and a switch (7) having a switching device which changes electrical connection with the electrodes between the alternating-current power supply (5) and the direct current pulsed power supply (6).

As the waveform of the alternating voltage output from the alternating-current power supply (5), a sine-wave waveform is generally used if not otherwise specified. The cell fusion chamber is divided into two compartments by a partition wall (35) formed by an insulator such as a silicone resin or the like. In the partition wall (35), a fine pore (9) having a minimum diameter of 1 µm to several tens of µm is formed. Cell A (10) and Cell B (11) are each contained in a cell suspension placed in the cell fusion region of the cell fusion chamber.

The performance in the above-mentioned example will be explained using FIG. 2 to FIG. 4. First of all, the switch (7) of the electronic power supply (4) is connected to the alternating-current power supply (5), which outputs a high-frequency voltage with an electrical field strength of approximately 400 V/cm to 700 V/cm and a frequency of 1 MHz. In this state, lines of electric force (12) concentrate at the fine pore (9), as shown in FIG. 2. Cell A (10) and Cell B (11) are affected by a dielectrophoretic force caused by the lines of electric force (12), and they are transferred to near the center portion of the fine pore (9), as shown in FIG. 3. Thus, Cell A (10) and Cell B (11) come into contact with each other. Next, the switch (7) of the electronic power supply (4) is switched to the direct current pulsed power supply (6). In Cell A (10) and Cell B (11), which are left in the state as shown in FIG. 3, the cellular membranes thereof are reversibly disrupted by the voltage pulsed direct current at the contact point of Cell A (10) and Cell B (11), and then reconstituted. Thus, a fused cell (hybridoma) is produced, as shown in FIG. 4. According to this, Cell A (10) and Cell B (11) can be fused at the fine pore.

However, the method for cell fusion using the cell fusion chamber disclosed in Patent Document 2 has a problem in that when the diameter of the fine pore is larger than those of Cell A (10) and Cell B (11), the probability of Cell A (10) and Cell B (11) making contact at the fine pore (9) in the same direction as those of the lines of electric force as shown in FIG. 30 becomes low, and so the probability of cell fusion decreases. On the other hand, when the diameter of the fine pore is smaller than those of Cell A (10) and Cell B (11), although both of the cells are trapped by the fine pore (9), make contact with each other, and are fused, the fused cell cannot be separated from the fine pore (9) as shown in FIG. 31. Accordingly, when the fused cell is collected by pulling it by force, the fused cell may be destroyed.

Moreover, the method for cell fusion using the cell fusion chamber disclosed in Patent Document 2 has another problem in that it is difficult to fix the two cells in the fine pore at the same time. For example, when a cell suspension containing Cell B (11) is introduced in the cell fusion chamber so as to place Cell B (11) in the fine pore after Cell A (10) is placed in the fine pore, Cell A (10) placed in the fine pore in advance is separated from the fine pore by introducing the cell suspension. Also, fixation of Cell A (10) and Cell B (11) in the fine pore at the same time requires skill and is quite difficult. Moreover, when plural cells are fused at the same time according to the method disclosed in Patent Document 2, plural pairs of two cells are required to be fixed in plural fine pores formed in an array state on an insulator.

The array means the state in which plural fine pores are disposed at even longitudinal and horizontal intervals. However, there is a problem in that when an alternating-current power supply is connected so as to fix cells in the fine pores, some of the fine pores include a concentration of plural cells fixed therein, while some of the fine pores includes no cells fixed therein. Accordingly, it is quite difficult to fuse the objective plural pairs of two cells in the plural fine pores formed in the array state.

In contrast, a method in which cells are singly fixed in plural fine pores formed in an array state has been reported (see, for example, Patent Document 3 (Japanese Patent Granted Publication No. 3723882)). According to the method disclosed in Patent Document 3, a step of adding a suspension containing plural cells to cover plural fine pores (corresponding to "microwells" in Patent Document 3) of which the inside diameter and depth are within a range from equal to twice as large as those of the cells (corresponding to "test lymphocytes") and waiting until the cells sink in the fine pores, and a step of washing out cells outside the fine pores are repeatedly conducted so as to fix a single cell in each fine pore.

However, the method in which a single cell is fixed in each fine pore as disclosed in Patent Document 3 has problems in that a long waiting time, approximately 5 minutes, is required until the cell sinks by gravity, the manipulation thereof is complicated and requires additional times for repeatedly conducting the steps of waiting until the cells sink in the fine pores and washing out the cells outside the fine pores, and it is difficult to effectively use all cells because some of the cells may be lost during the step of washing out the cells outside the fine pores. In general, when cell fusion is carried out, it is preferable to shorten the treatment time as much as possible, for the purpose of maintaining the activity of the cells, and to prevent the loss of cells as much as possible, for the purpose of finding the specificity possessed by the respective cells.

SUMMARY OF THE INVENTION

The present invention relates to a cell fusion chamber in which two types of cells having different diameters are fused, the cell fusion chamber including: a cell fusion region in which cell fusion is carried out; a pair of electrodes formed by a conductor and disposed opposite to each other in the cell fusion region; and a partition wall disposed between the pair of electrodes to divide the cell fusion region into two compartments, the partition wall having at least one fine pore penetrating through the partition wall in a direction of the pair of electrodes; in which a diameter of the fine pore is smaller than that of the cell having a larger diameter than the other cell and is larger than that of the cell having a smaller diameter than the other cell.

The cell fusion chamber may further include: an alternating-current power supply which applies an alternating voltage to the electrodes; a direct current pulsed power supply which applies a voltage pulsed direct current to the electrodes; and a switching device which connects the electrodes with the alternating-current power supply or the direct current pulsed power supply.

The cell fusion chamber may further include: a device which flows a suspension containing the cells into the cell fusion region.

Moreover, the present invention relates to a cell fusion method using the cell fusion chamber, which includes: separately introducing two types of cells having different diameters into each compartments of the cell fusion region divided by the partition wall; drawing the cells to the fine pore of the partition wall by applying an alternating voltage from the alternating-current power supply to the electrodes; switching a connection with the electrodes from the alternating-current power supply to the direct current pulsed power supply using the switching device after drawing the cells; fusing the cells by applying a voltage pulsed direct current from the direct current pulsed power supply to the electrodes; and transferring the fused cell in a direction from the compartment into which the cell having a smaller diameter is introduced to the compartment into which the cell having a larger diameter is introduced.

Moreover, the present invention relates to a cell fusion device including: a cell fusion container including: a cell fusion region in which cell fusion is carried out; a pair of electrodes formed by a conductor and disposed opposite to each other in the cell fusion region; a tabular spacer disposed between the pair of electrodes; and a tabular insulator disposed between the spacer and one of the electrodes and having at least one fine pore penetrating through the insulator in a direction of the pair of electrodes; and an electronic power supply which applies an alternating voltage or a voltage pulsed direct current to the pair of electrodes, in which the insulator is disposed on a cell fusion region side-surface of one of the electrodes.

In the cell fusion device, the electronic power supply may include: an alternating-current power supply which applies an alternating voltage to the pair of electrodes; a direct current pulsed power supply which applies a voltage pulsed direct current to the pair of electrodes; and a switching device which connects the electrodes with the alternating-current power supply or the direct current pulsed power supply.

In the cell fusion device, the fine pore may have a shape which traps a single cell.

In the cell fusion device, the electronic power supply may apply to the electrodes an alternating voltage having a waveform fixing a single cell in each fine pore.

In the cell fusion device, the electronic power supply may apply to the electrodes an alternating voltage having a waveform periodically repeating charge and discharge of cells.

In the cell fusion device, the electronic power supply may apply to the electrodes an alternating voltage having a waveform including per half cycle thereof at least one plateau in which a predetermined voltage at a level other than 0 is maintained for a predetermined time.

In the cell fusion device, the electronic power supply may apply to the electrodes an alternating voltage having a waveform selected from the group consisting of a rectangular wave waveform, a trapezoidal wave waveform, and a waveform combining a rectangular wave with a trapezoidal wave.

In the cell fusion device, the electronic power supply may apply to the electrodes an alternating voltage having a waveform including a plateau in which a predetermined voltage at a level other than 0 is maintained for a predetermined time which is no shorter than a time constant calculated by multiplying a cellular capacitance by a resistance of a cell suspension containing the cells.

In the cell fusion device, a diameter of a maximum circle inscribed in a planar shape of the fine pore may be no less than equal to but less than twice as large as that of a cell to be fixed in the fine pore and a depth of the fine pore may be no larger than the diameter of the cell to be fixed in the fine pore.

In the cell fusion device, the insulator may have plural fine pores in the face thereof, each fine pore being formed evenly spaced apart from adjacent fine pores.

In the cell fusion device, the plural fine pores may be formed in the face of the insulator in an array state.

In the cell fusion device, the distance between the adjacent fine pores may be no less than 0.5 times but less than 6 times as large as a diameter of a cell to be fixed in the respective fine pores.

In the cell fusion device, a spacer may include: a through-hole forming the cell fusion region.

In the cell fusion device, the spacer may include: an introducing channel through which a cell is introduced; and an exhausting channel through which the cell is exhausted.

Moreover, the present invention relates to a cell fusion method using the cell fusion device, which includes: introducing a first cell into the cell fusion region; fixing the introduced first cell in the fine pore by applying an alternating voltage to the electrodes; introducing a second cell into the cell fusion region after fixing the first cell; bringing the introduced second cell in contact with the first cell at the fine pore by applying the alternating voltage to the electrodes; and fusing the first and second cells making contact by applying a voltage pulsed direct current.

In the cell fusion method, the alternating voltage may be an alternating voltage having any one of the waveforms described above.

In the cell fusion method, the first cell and the second cell can be fused at a farthest position of the fine pore from the bottom of the fine pore.

In the cell fusion method, the first cell may have a diameter smaller than that of the second cell.

DETAILED DESCRIPTION OF THE INVENTION

Figure 1:
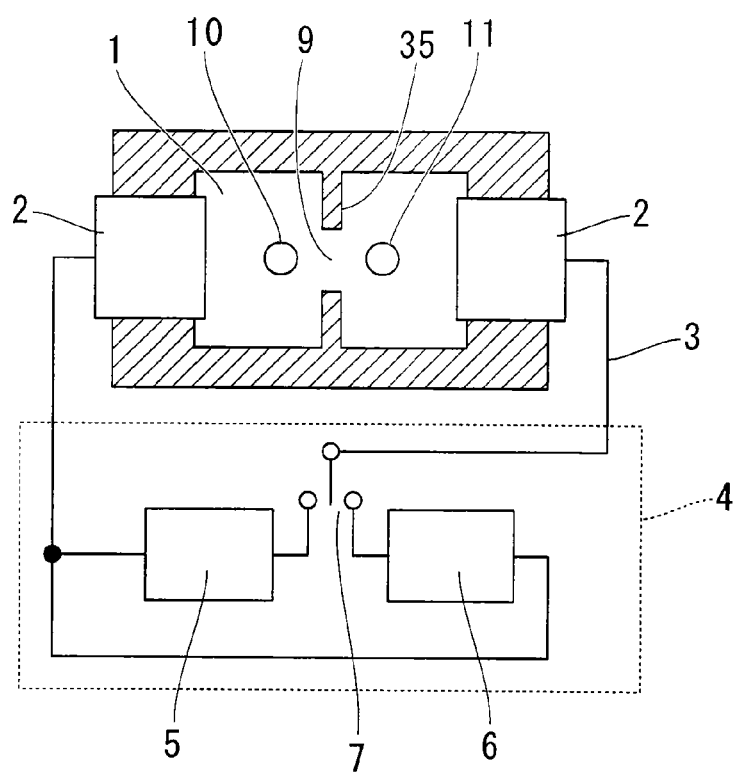
FIG. 1 is a schematic diagram showing a cross-sectional view of a cell fusion chamber described in Patent Document 1.

An object of the present invention is to provide a novel cell fusion chamber and a novel cell fusion device which effectively and reliably enable two cells to electrically fuse and to provide a cell fusion method using the same.

As a result of diligent studies, the inventors of the present invention have found that the following solves the above-mentioned problems, and have completed the present invention.

A first embodiment of the present invention which enables the above-mentioned problems to be solved is a cell fusion chamber in which two types of cells having different diameters are fused, the cell fusion chamber including: a cell fusion region in which cell fusion is carried out; a pair of electrodes formed by a conductor and disposed opposite to each other in the cell fusion region; and a partition wall disposed between the pair of electrodes to divide the cell fusion region into two compartments, the partition wall having at least one fine pore penetrating through the partition wall in a direction of the pair of electrodes, and the fine pore having a diameter no larger than that of the cell having a larger diameter than the other cell and no smaller than that of the cell having a smaller diameter than the other, and a cell fusion method including: separately introducing two types of cells having different diameters into each compartments of the cell fusion region; drawing the cells to the fine pore by applying an alternating voltage; fusing the cells by applying a voltage pulsed direct current; and transferring the fused cell in a direction from the compartment into which the cell having a smaller diameter is introduced to the compartment into which the cell having a larger diameter is introduced.

A second embodiment of the present invention which enables the above-mentioned problems to be solved is a cell fusion device including: a cell fusion container including: a cell fusion region; a pair of electrodes formed by a conductor and disposed opposite to each other in the cell fusion region; a spacer disposed between the pair of electrodes; an insulator disposed between a spacer and one of the electrodes and having at least one fine pore penetrating through the insulator in a direction of the pair of electrodes; and an electronic power supply including: an alternating-current power supply which applies an alternating voltage to the electrodes; and a direct current pulsed power supply which applies a voltage pulsed direct current to the electrodes; in which the waveform of the alternating voltage is a waveform periodically repeating charge and discharge of cells, and a cell fusion method using the cell fusion device, which includes: introducing a first cell into the cell fusion region; fixing the introduced first cell in the fine pore by applying an alternating voltage; introducing a second cell into the cell fusion region after that; bringing the introduced second cell in contact with the first cell at the fine pore by applying the alternating voltage; and fusing the first and second cells making contact by applying a voltage pulsed direct current.

In the following, the cell fusion chamber, the cell fusion device, and the cell fusion method using the same according to the present invention will be explained in further detail using drawings.

Figure 32:
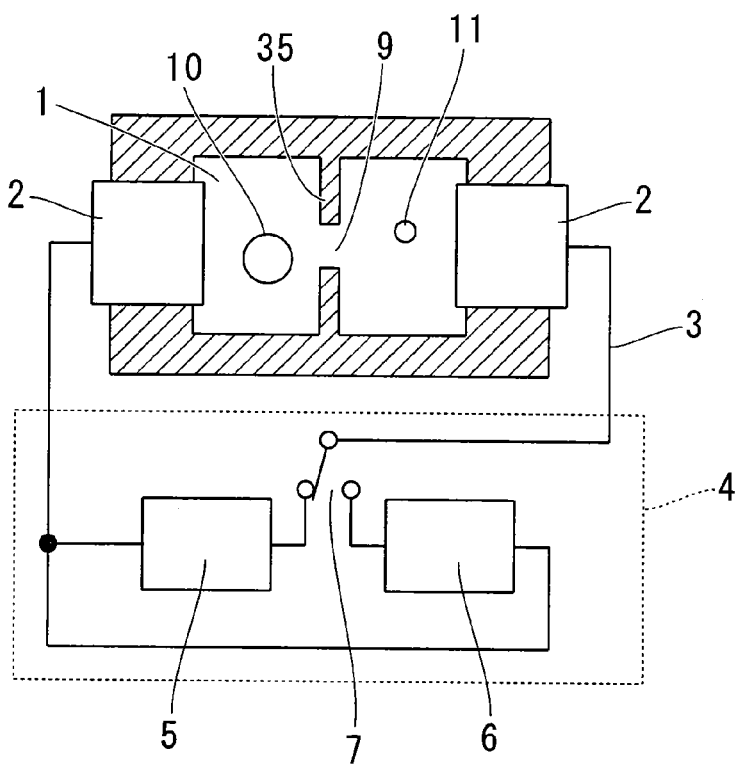
FIG. 32 is a schematic diagram showing a cross-sectional view of an embodiment of a cell fusion chamber according to the present invention.

FIG. 32 is a schematic diagram showing a cross-sectional view of a cell fusion chamber according to the present invention. In FIG. 32, at both sides of a cell fusion region (1) of the cell fusion chamber formed by a resin or the like, electrodes (2) formed by a conductor are disposed. These electrodes (2) are connected to an electronic power supply (4) disposed outside via a conductor (3). The electronic power supply (4) includes: an alternating-current power supply (5) which outputs a high-frequency alternating voltage with an electrical field strength of approximately 400 V/cm to 700 V/cm and a frequency of approximately 1 MHz; a direct current pulsed power supply (6) which outputs a voltage pulsed direct current with an electrical field strength of approximately 7 kV/cm and a pulse width of 50 micro seconds; and a switch (7) which changes an electrical connection with the electrodes between the alternating-current power supply (5) and the direct current pulsed power supply (6). In the cell fusion chamber, the cell fusion region (1) is divided into two compartments by a partition wall (35) formed by an insulator such as a silicone resin, or the like. The partition wall (35) may be integrally formed with the cell fusion region (1). Alternatively, the partition wall (35) may be formed independently from the cell fusion region (1) using an insulator, and then fixed by fixing edges of the partition wall (35) placed in a position dividing the cell fusion region (1) into two compartments using an adhesive agent or the like or by putting the partition wall (35) in the cell fusion region (1) so as to divide the cell fusion region (1) into two compartments and bonding the compartments via the partition wall (35) with pressure. Cell A (10) and Cell B (11) are respectively contained in cell suspensions placed in the cell fusion region (1) of the cell fusion chamber.

In the partition wall (35), a fine pore (9) having a minimum diameter of 1 μm to several tens of μm is formed. When the diameter of Cell A (10) is larger than that of Cell B (11), the fine pore (9) is formed to have a diameter which is smaller than that of Cell A (10) and larger than that of Cell B (11).

Two types of cells to be fused, such as, for example, a combination of a spleen cell and a myeloma cell used for producing a monoclonal antibody, have different diameters from each other. The diameter of the fine pore (9) is not particularly limited provided that the diameter is no more than the diameter of the cell having a larger diameter and no less than the diameter of the cell having a smaller diameter. Although the diameter of the fine pore (9) means the diameter of a circle when the shape of the fine pore (9) is a circle, the diameter of the fine pore (9) means the length of a longer diagonal line of a quadrangle when the shape of the fine pore (9) is a quadrangle.

Although the thickness of the partition wall (35) is not particularly limited, the thicknesses may be determined in accordance with the dimension of the cell fusion chamber in which the cells are placed or the like, and the dimension ratio of the compartments of the cell fusion chamber divided by the partition wall (35) may be determined in accordance with the dimension of the cells used. A raw material of the partition wall (35) may be an insulating material such as a glass, a polymer resin, or the like. Moreover, it is possible to fuse plural cells at the same time by enlarging an area of the electrodes (2) and forming plural fine pores (9) in the partition wall (35).

Figure 33:
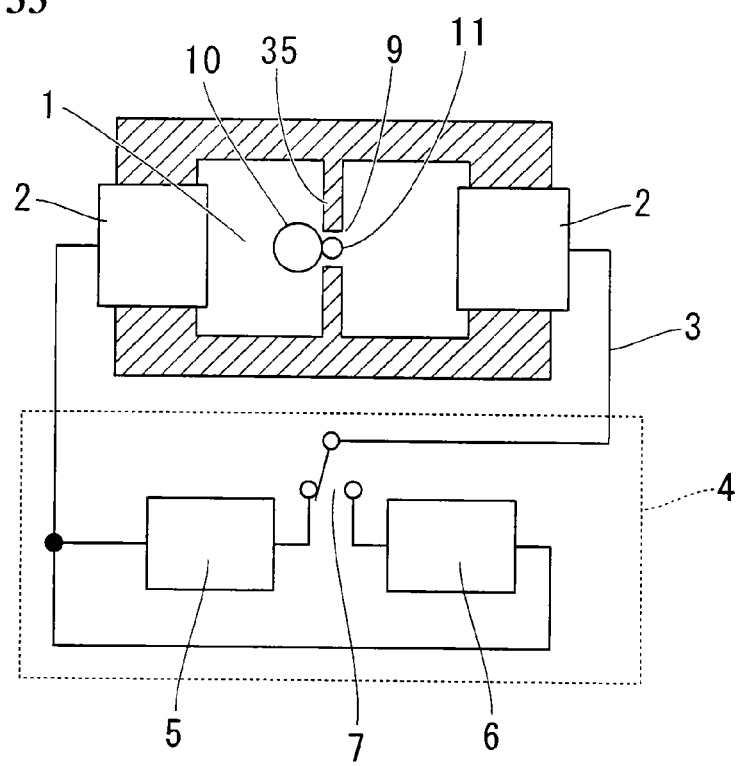
FIG. 33 is a first drawing illustrating the performance of a cell fusion chamber according to the present invention.
Figure 34:
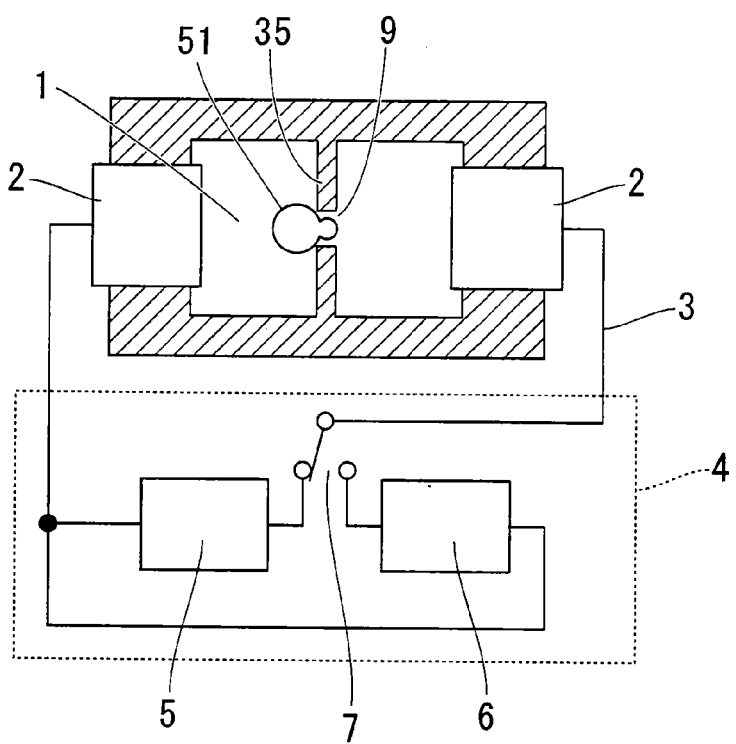
FIG. 34 is a second drawing illustrating the performance of a cell fusion chamber according to the present invention.
Figure 35:
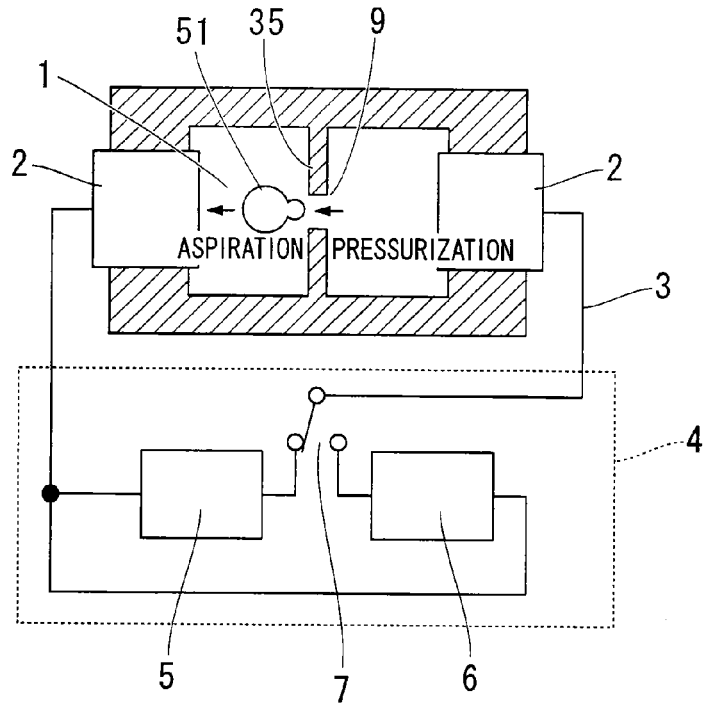
FIG. 35 is a third drawing illustrating the performance of a cell fusion chamber according to the present invention.

Next, the performance according to the present invention will be more specifically explained using FIGS. 33 to 35. First of all, the switch (7) of the electronic power supply (4) is connected to the alternating-current power supply (5) which outputs a high-frequency voltage with an electrical field strength of approximately 400 V/cm to 700 V/cm and a frequency of 1 MHz. Cell A (10) and Cell B (11) are affected by a dielectrophoretic force caused by lines of electric force concentrating in the fine pore (9), and so drawn near the center of the fine pore (9), as shown in FIG. 33. Since the diameter of Cell A (10) is larger than that of the fine pore (9), Cell A (10) is trapped so as to cover the fine pore (9). In contrast, since the diameter of Cell B (11) is smaller than that of the fine pore (9), Cell B (11) passes through the fine pore (9) and reliably makes contact with Cell A (10) in a direction of the line of electric force.

Next, the switch (7) of the electronic power supply (4) is changed to connect to the direct current pulsed power supply (6). Cellular membranes of Cell A (10) and Cell B (11) placed in a state as shown in FIG. 33 are changed (this change being presumed as reversible disruption) at the contact point thereof by applying the voltage pulsed direct current, as a result of which Cell A (10) and Cell B (11) are fused as shown in FIG. 34. Thus, Cell A (10) and Cell B (11) can be reliably fused by making Cell A (10) and Cell B (11) come into contact at the fine pore (9) in the same direction as that of lines of electric force.

In order to easily pull out the fused cells as shown in FIG. 35, a device which flows a suspension containing the fused cell of Cell A (10) and Cell B (11) by sucking the suspension from the side of the chamber introducing Cell A (10) or by pressurizing the suspension from the side of the chamber introducing Cell B (11) may be used. That is, Cell A (10) having a larger diameter and Cell B (11) having a smaller diameter are respectively introduced from both sides of the chamber into the compartments divided by the partition wall (35), and the alternating voltage is applied to these cells near the fine pore (9) to fuse the cells, followed by transferring the fused cells in a direction from the compartment into which the cell having a smaller diameter is introduced to the compartment into which the cell having a larger diameter is introduced.

In the following, the cell fusion device according to the present invention and the cell fusion method using the same will be explained in more detail using the drawings.

The cell fusion device according to the present invention includes a cell fusion container containing: a cell fusion region in which cell fusion is carried out; a pair of electrodes formed by a conductor and disposed opposite to each other in the cell fusion region; a tabular spacer disposed between the pair of electrodes; and a tabular insulator disposed between the spacer and one of the electrodes and having at least one fine pore penetrating through the insulator in a direction of the pair of electrodes; and an electronic power supply which applies an alternating voltage or a voltage pulsed direct current to the pair of electrodes. Moreover, the electronic power supply may include: an alternating-current power supply which applies an alternating voltage to the pair of electrodes; a direct current pulsed power supply which applies a voltage pulsed direct current to the pair of electrodes; and a switching device which connects the electrodes with the alternating-current power supply or the direct current pulsed power supply.

Figure 5:
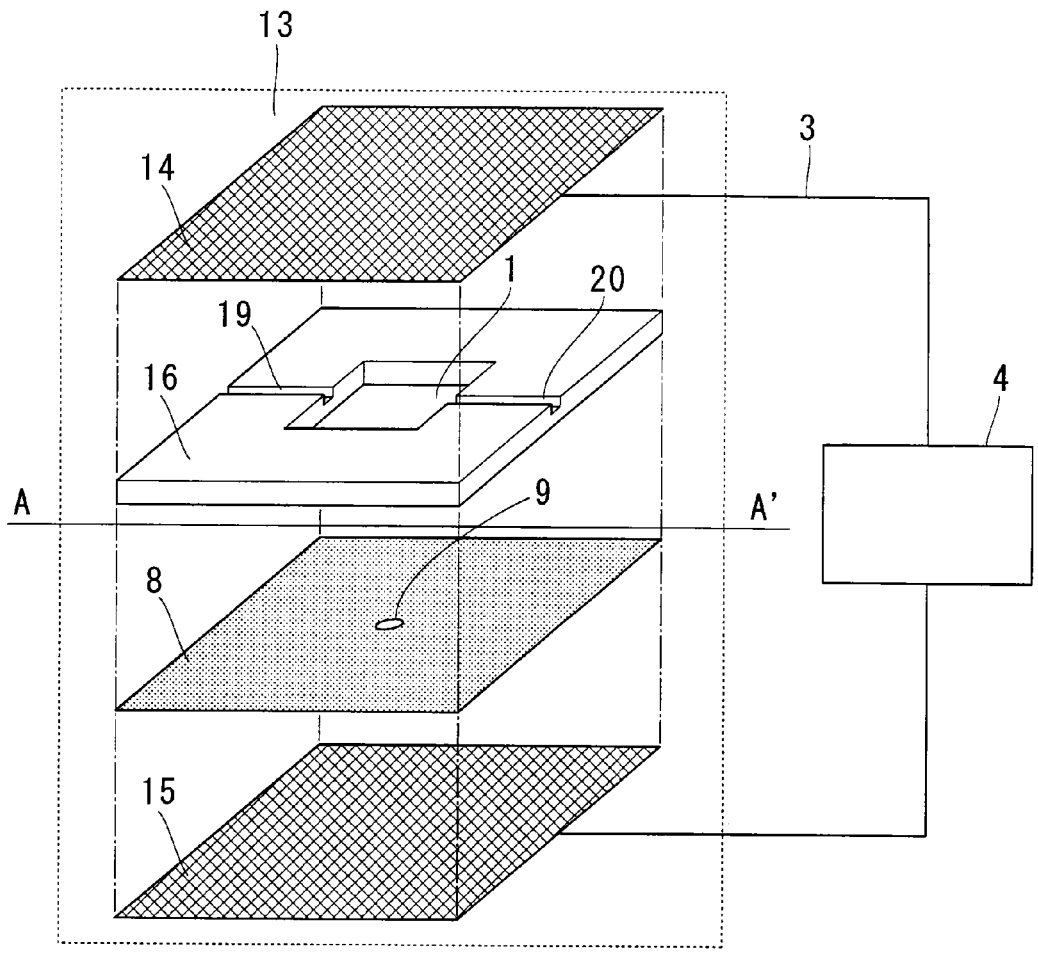
FIG. 5 is a schematic diagram showing an embodiment of a cell fusion device according to the present invention.

FIG. 5 is a schematic diagram showing the cell fusion device according to the present invention. The cell fusion device according to the present invention is mainly composed of a cell fusion container (13) and the electronic power supply (4).

The cell fusion container has a structure as shown in FIG. 5 in which a spacer (16) is disposed between an upper electrode (14) and a lower electrode (15), and an insulator (8) having the fine pore (9) is disposed between the spacer (16) and the lower electrode (15). Raw materials used for forming the upper electrode (14) and the lower electrode (15) are not particularly limited, provided that the raw materials are conductors that are chemically stable, such as metals such as platinum, gold, copper, or the like, alloys such as stainless steel, or the like, glass substrates produced by forming films using transparent conductive materials such as ITO (Indium Tin Oxide) or the like. Among them, glass substrates produced by forming films using transparent conductive materials such as ITO are preferably used in order to observe the process of cell fusion.

Although the dimensions of the upper electrode (14) and the lower electrode (15) are not particularly limited, it is preferable that the dimensions be 70 mm in length, 40 mm in breadth, and 1 mm in thickness of 1 mm in view of ease of handling.

The spacer (16) is disposed so that the upper electrode (14) and the lower electrode (15) do not directly make contact, the spacer (16) having a through-hole so as to ensure a space forms in the cell fusion container of the cell fusion region in which a cell suspension is placed, and the spacer (16) being formed by an insulating material such as glass, ceramic, resin, or the like. In the spacer (16), an introducing channel through which the cells are introduced into the cell fusion container, an inlet (19) communicating with the introducing channel, an exhausting channel through which the cells are exhausted, and an outlet (20) communicating with the exhausting channel may be disposed. Although the dimension of the spacer (16) is not particularly limited unless the upper electrode (14) and the lower electrode (15) make contact with each other, it is preferable that the dimension be determined in accordance with that of the electrodes. For example, when the dimension of the electrode is about 70 mm in length and 40 mm in breadth, the dimension of the spacer (16) is preferably about 40 mm in length and 40 mm in breadth. The dimension of the through-hole (inner space) of the spacer (16) forming the cell fusion region (1) and the thickness of the through-hole (or the spacer (16)) are not particularly limited provided that the through-hole can hold approximately a few microliters to milliliters of the cell suspension. For example, when the dimension of the spacer (16) is about 40 mm in length and 40 mm in breadth, the dimension of the through-hole of the spacer (16) is preferably about 20 mm in length and 20 mm in breadth and the thickness of the spacer (16) is preferably about 0.5 to 2.0 mm.

In the insulator (8), the fine pore (9) is formed. Any raw materials can be used for forming the insulator (8), provided that the raw materials are insulating materials such as glass, ceramic, resin, or the like. However, since the insulator (8) is required to be processed to have the fine pore (9) perforating therethrough, materials which can be relatively easily processed, such as resin or the like are preferably used. As a method for forming the fine pore (9) perforating through the resin, a method in which laser beams are irradiated onto a position in which the fine pore is to be formed, a method for molding using a metal mold having a pin so as to form a fine through-hole at the position of the fine pore, or other known methods may be used. When an UV-curable resin is used as the insulating material, the fine pore may be formed by carrying out conventional photolithography (exposure) and etching (developing) using an exposure photomask in which a pattern corresponding to the fine pore is formed. In order to form plural fine pores in the insulator, the UV-curable resin is preferably used as the insulating material with the conventional photolithography and etching technique.

Figure 6:
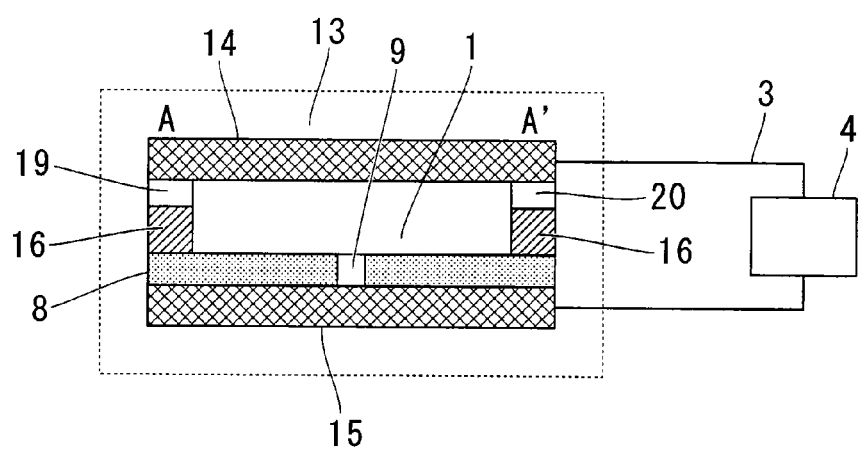
FIG. 6 is a cross-sectional drawing of AA' portion of a cell fusion container of the device shown in FIG. 5.

FIG. 6 is a schematic view showing a cross-sectional view of AA' region of the cell fusion container shown in FIG. 5. In order to laminate the upper electrode (14), the spacer (16), the insulator (8), and the lower electrode (15) as shown in FIG. 6, a method in which they are adhered together with an adhesive agent, a method in which they are heat-sealed under pressure, a method in which the spacer (16) is formed using a resin having a surface stickiness such as PDMS (poly-dimethylsiloxane), silicone sheet, or the like, or other known methods may be used. Thus, the cell fusion region (1) shown in FIG. 6 can be formed.

To the upper electrode (14) and the lower electrode (15) of the cell fusion container, the electronic power supply (4) is connected through the conductor (3). The electronic power supply (4) is composed of the alternating-current power supply (5) which applies an alternating voltage between the upper electrode (14) and the lower electrode (15) and the direct current pulsed power supply (6) which applies a voltage pulsed direct current between the upper electrode (14) and the lower electrode (15) so as to fuse the cells. The connection with the electrodes can be arbitrarily changed between the alternating-current power supply (5) and the direct current pulsed power supply (6) using a switching device such as the switch (7) or the like.

Moreover, it is preferable that the insulator (8) of the cell fusion device has plural fine pores (9) in the face thereof, each fine pore (9) being formed evenly spaced apart from adjacent fine pores. For example, it is preferable that the fine pore-array (9) is formed in the face of the insulator (8).

Figure 7:
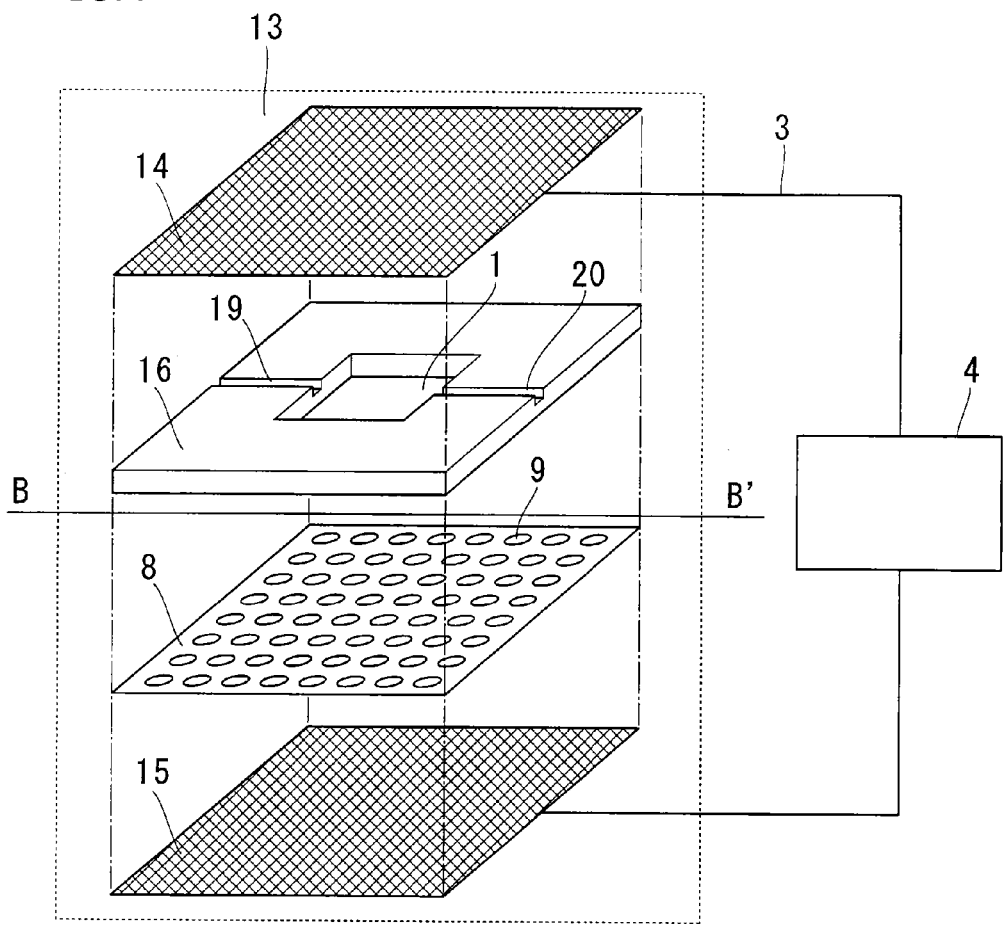
FIG. 7 is a schematic diagram of another embodiment of a cell fusion device according to the present invention used in Example 2.
Figure 8:
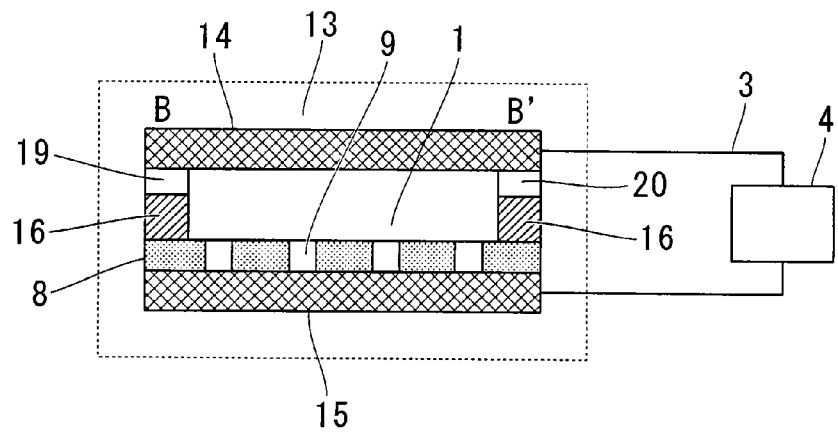
FIG. 8 is a cross-sectional drawing of BB' portion of a cell fusion container in the device shown in FIG. 7.

FIG. 7 is a schematic view showing a cell fusion device in which plural fine pores (9) are formed in the insulator (8) in an array state. FIG. 8 is a schematic view showing a cross-sectional view of BB' region of the cell fusion container shown in FIG. 7.

The array state means that the plural fine pores are formed so that the longitudinal and horizontal distances between respective adjacent fine pores are approximately equal. In the case of the fine pore-array, an electrical field is approximately evenly created in all of the fine pores by the voltage applied to the electrodes. In order to fix a single cell in each fine pore, it is preferable that the distance between the adjacent fine pores formed in the array state be neither extremely narrow nor extremely large. When the distance between the adjacent fine pores is extremely narrow, the probability of fixing plural cells in each fine pore increases, as a result of which the probability of generating fine pores having no fixed cells increases. When the distance between the adjacent fine pores is extremely large, some of the cells remain between the fine pores, and so the probability of generating fine pores having no fixed cells increases. Accordingly, it is specifically preferable that the distance between the adjacent fine pores be no less than 0.5 times but less than 6 times, more preferably approximately within a range from equal to twice, as large as the diameter of a cell to be fixed in the respective fine pores.

In the following, the waveform of the alternating voltage and the shape of the fine pore which enable a single cell to be fixed in each fine pore will be explained.

In an embodiment of the cell fusion device according to the present invention, the electronic power supply applies to the electrodes an alternating voltage having a waveform which enables a single cell to be fixed in each fine pore, the waveform periodically repeating charge and discharge of the cells. Preferably, the waveform of the alternating voltage has per half cycle thereof at least one plateau in which a predetermined voltage at a level other than 0 is maintained for a predetermined time. For example, the waveform of the alternating voltage is a waveform selected from the group consisting of a rectangular wave, a trapezoidal wave, and a waveform combining these. Preferably, the predetermined time in which a predetermined voltage at a level other than 0 is maintained is no shorter than a time constant calculated by multiplying a cellular capacitance by a resistance of a cell suspension containing the cells.

In an embodiment of the cell fusion device according to the present invention, the diameter of a maximum circle inscribed in a planar shape of the fine pore is no less than equal to and less than twice as large as that of the cell to be fixed in the fine pore and the depth of the fine pore is no larger than the diameter of the cell to be fixed in the fine pore. Moreover, the distance between the adjacent fine pores is no less than 0.5 times but less than 6 times as long the diameter of the cell to be fixed in the fine pore.

When the alternating voltage with the above-mentioned waveform is applied or the fine pore is formed in the above-mentioned shape, it is possible for a single cell to be more reliably fixed in each fine pore, another cell to be further fixed onto the fixed cell, and thus two cells contact at the fine pores to fuse two cells.

Figure 9:
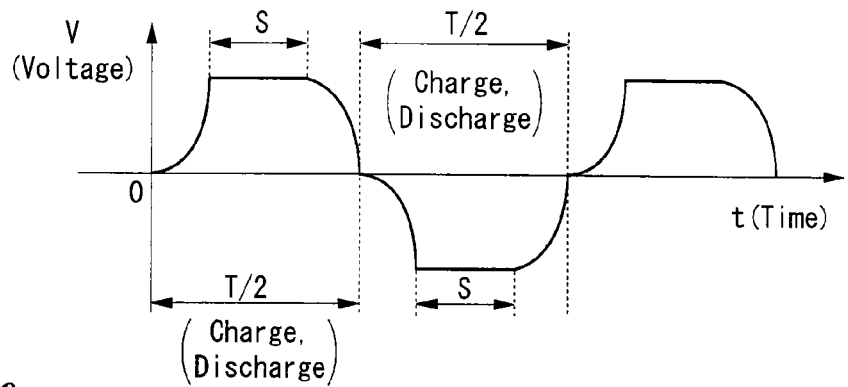
FIG. 9 is a drawing showing an example of a waveform of an alternating voltage used in the present invention.

The waveform of the alternating voltage used in the cell fusion device according to the present invention is not particularly limited, provided that it enables charge and discharge of the cells to periodically repeat. FIG. 9 shows an embodiment of such a waveform of the alternating voltage. In FIG. 9, charge and discharge of the cells are repeated per half cycle T/2 of the waveform of the alternating voltage. In the case of FIG. 9, the positive and negative polarities of the voltage are inverted per half cycle, and so the polarity of the charged cell is inverted between a positive charge and a negative charge per half cycle.

It is preferable that the waveform of the alternating voltage used in the cell fusion device according to the present invention does not contain a direct current component. The reason for this is that the direct current component makes it difficult for a dielectrophoretic to control the motion of the cells, draw the cells to the fine pores, and fix the cells in the fine pores, by generating an electrostatic force which provides the cells with a disproportionate force which transfers the cells toward a particular direction, or by causing ions contained in the cell suspension to electrically react on the surface of the electrodes and generate heat which causes thermal motion of the cells.

More specifically, the waveform of the alternating voltage used in the cell fusion device according to the present invention is a waveform having per half cycle thereof at least one plateau in which a predetermined voltage at a level other than 0 is maintained for a predetermined time. In FIG. 9, S (second) indicates the predetermined time in which the voltage level has not been changed. It is preferable that the predetermined time S [s] be no shorter than a time constant $\tau$ [s] calculated by multiplying a cellular capacitance C [F] by a resistance R ($\Omega$) of the cell suspension, and so satisfies the following formula:

$$S \geq \tau (= C \times R).$$

Figure 10:
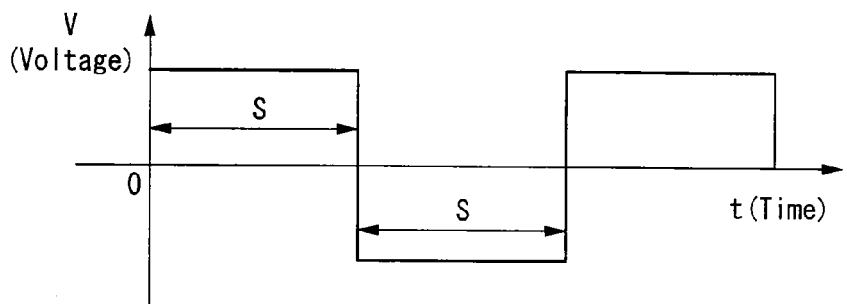
FIG. 10 is a drawing showing a rectangular wave as another example of a waveform of an alternating voltage used in the present invention.
Figure 11:
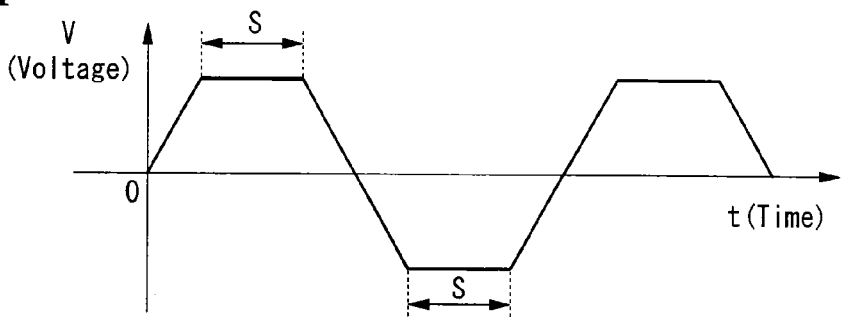
FIG. 11 is a drawing showing a trapezoidal wave as another example of a waveform of an alternating voltage used in the present invention.

The waveform of the alternating voltage is not limited to the waveform shown in FIG. 9, and it is apparent that changes and modifications may be arbitrarily made therein without departing from the scope of the present invention. For example, the waveform of the alternating voltage may be a rectangular wave (shown in FIG. 10), a trapezoidal wave (shown in FIG. 11), or a waveform combining these waves (shown in FIG. 12). The level and frequency of the voltage to be applied are suitably determined in accordance with the distance between the electrodes of the cell fusion container, types or dimensions of the cells to be fused, and types of liquid components of the cell suspension. For example, when the dimension of the cell fusion container is approximately 2 cm×2 cm, the distance between the electrodes is approximately 1 mm, the diameter of the cell to be fused is approximately 10 μM, and the type of liquid component of the cell suspension is 300 mM of a mannitol aqueous solution, the cellular capacitance is generally approximately 1 pF, and the resistance value of the cell suspension is approximately 5 kΩ, and thus the time constant τ [s] calculated by multiplying the cellular capacitance by the resistance is 5 nS. Accordingly, it is preferable that the waveform of the alternating voltage applied to the electrodes be an alternating voltage waveform having per half cycle thereof at least one plateau in which a predetermined voltage at a level other than 0 is maintained for 5 ns or longer. For example, when the waveform of the alternating voltage is a rectangular wave as shown in FIG. 10, it is preferable that the predetermined time be longer than 5 ns, that is, the frequency be less than 100 MHz (=1/(2×5 ns)), more preferably the frequency be approximately 1 to 3 MHz in view of the ease of electrical handling thereof and ease of generation using a commercially available signal generator. In this case, it is preferable that the alternating voltage with the rectangular wave be approximately 10 to 20 Vpp in order to generate a dielectrophoretic force in an amount sufficient to draw the cells to the fine pores. In this case, the time required for drawing the cells to the fine pores is approximately 1 to 5 second[s], and thus the cells can be instantaneously fixed in the fine pores.

Next, the reason a single cell is fixed in each fine pore when the alternating voltage with the above-mentioned waveform and the fine pore formed as described above are used will be explained using FIG. 13 to FIG. 23.

Figure 13:
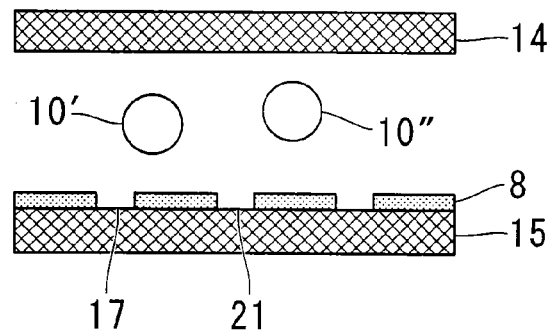
FIG. 13 is a first drawing illustrating cell handling in a method for cell fusion according to the present invention.
Figure 14:
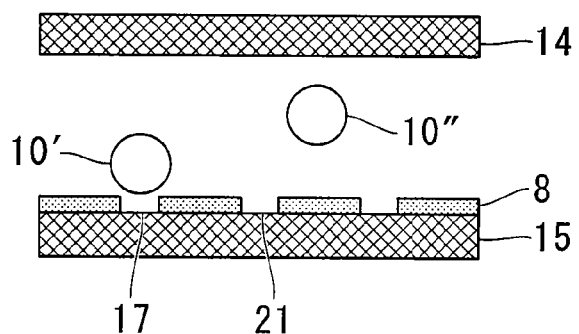
FIG. 14 is a second drawing illustrating cell handling in a method for cell fusion according to the present invention.
Figure 15:
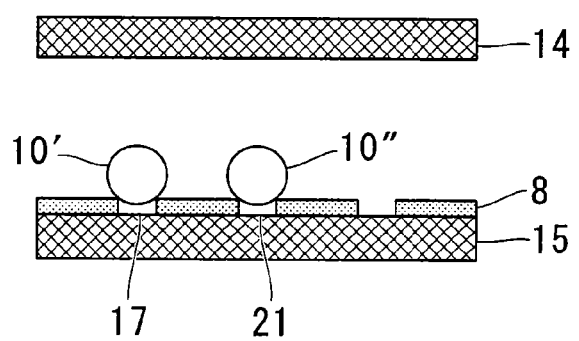
FIG. 15 is a third drawing illustrating cell handling in a method for cell fusion according to the present invention.
Figure 16:
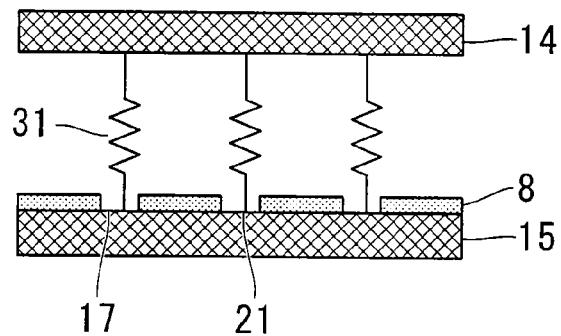
FIG. 16 is a drawing showing FIG. 13 by an electrical equivalent circuit.
Figure 17:
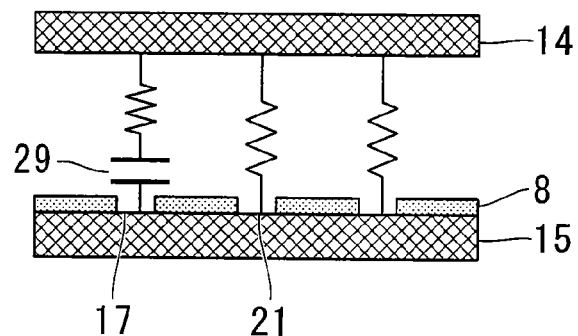
FIG. 17 is a drawing showing FIG. 14 by an electrical equivalent circuit.
Figure 18:
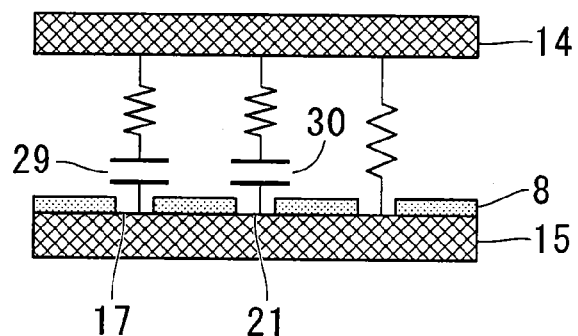
FIG. 18 is a drawing showing FIG. 15 by an electrical equivalent circuit.

FIG. 13 to FIG. 15 are schematic diagrams showing steps in which the cells enter the fine pores of the cell fusion device according to the present invention. The thickness of the insulator (8) is approximately equal to the diameters of Cell A' (10') and Cell A" (10"). The inside diameter of the fine pore is no less than equal to but less than twice as long as the diameters of Cell A' (10') and Cell A" (10"). In FIG. 14, after Cell A' (10') enters Fine pore A' (17), Cell A" (10") enters Fine pore A" (21). FIG. 16 to FIG. 18 are drawings respectively showing FIG. 13 to FIG. 15 by electrical equivalent circuits. In this drawings, the cell suspension containing the cells can be represented as a resistance (resistance value: 5 kΩ), and the cells can be represented as a condenser (capacitance: 1 pF).

Figure 19:
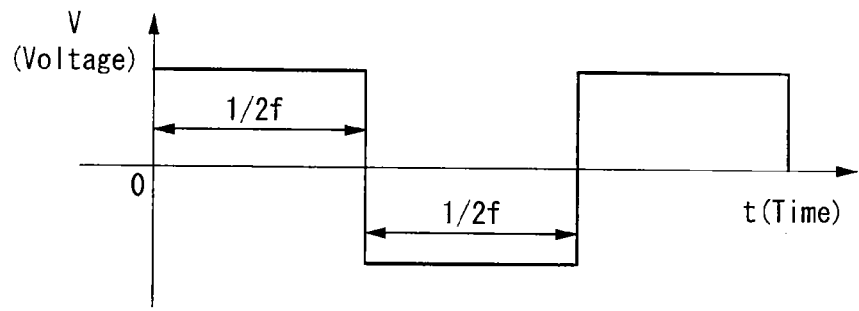
FIG. 19 is a drawing showing a waveform of a rectangular wave alternating voltage with frequency f [Hz].
Figure 20:
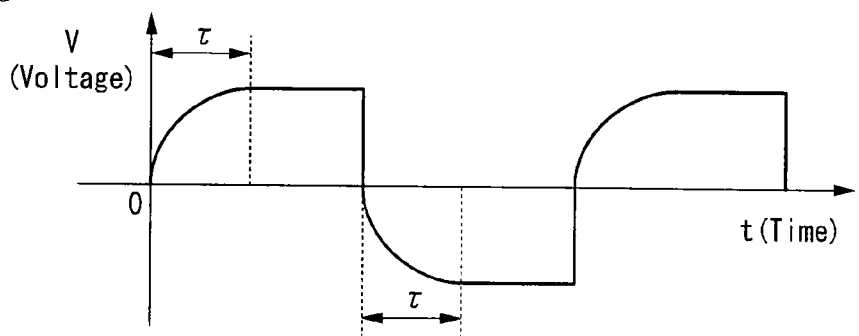
FIG. 20 is a drawing showing a voltage waveform of a Condenser A shown in FIG. 17, the waveform being output when a rectangular wave alternating voltage with frequency f [Hz] as shown in FIG. 19 is applied between electrodes.
Figure 21:
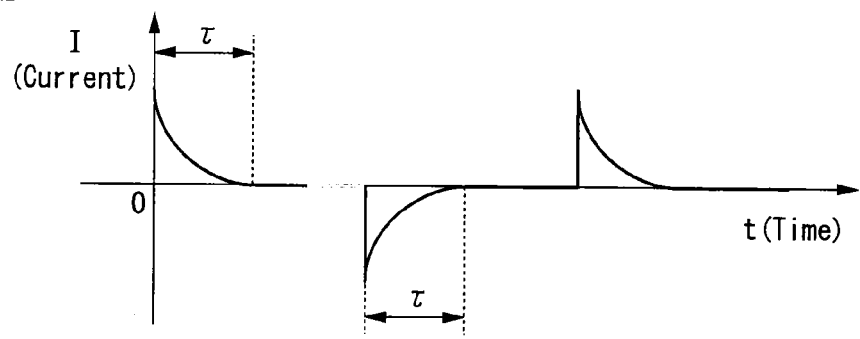
FIG. 21 is a drawing showing a current waveform of a Condenser A shown in FIG. 17, the waveform being output when a rectangular wave alternating voltage with frequency f [Hz] as shown in FIG. 19 is applied between electrodes.

When an alternating voltage having a rectangular waveform with frequency f [Hz] as shown in FIG. 19 is applied, lines of electric force are concentrated at the fine pore, and so a dielectrophoretic force is applied to the cells, as a result of which the cells are drawn to the fine pore. Thus, Cell A' (10') is fixed in Fine pore A' (17) and covers Fine pore A' (17), in the same manner as that shown in FIG. 2 to FIG. 3. The cells are drawn to the fine pores by gravity or an electrostatic force applied from the electrodes, in addition to the dielectrophoretic forces. The portion of Fine pore A' (17) covered with Cell A' (10') becomes electrically equivalent to Condenser A (29) as shown in FIG. 17. When the voltage with the waveform as shown in FIG. 19 is applied, the waveform of the voltage applied in Condenser A (29) is shown in FIG. 20, the current waveform is shown in FIG. 21. As shown in FIG. 20, Condenser A (29) can be charged by applying the voltage for a period of time constant τ [s] (=C×R) calculated by multiplying capacitance C [F] of Cell A (10) by resistance R [Ω] of the cell suspension containing the cell.

Since it is preferable that a period of the plateau in which a predetermined voltage other than 0 is maintained for a predetermined time be no less than the time constant calculated by multiplying a cellular capacitance by a resistance of the cell suspension containing the cells, it is preferable to apply an alternating voltage having a rectangular waveform with a frequency satisfying the following formula: $\tau \le \frac{1}{2} f$. When Condenser A (29) is charged, the current does not flow. Accordingly, the current flows to Condenser A (29) in a pulse state with flow durations of time constant τ, between which the current does not flow and so Condenser A becomes electrically equivalent to the insulator, as shown in FIG. 21. As a result, at Fine pore A' (17) in which Cell A' (10') is fixed, lines of electric force are not concentrated, and so the probability that Cell A' (10') draws another cell decreases. On the other hand, the lines of electric force are concentrated in Fine pore A" (21), and so the dielectrophoretic force transfers Cell A" (10") to Fine pore A" (21), as a result of which Cell A" (10") is fixed in and covers Fine pore A" (21). By repeating these, the cells continuously singly enter vacant fine pores, and thus a single cell is fixed in each fine pore.

When the inside diameter of the fine pore is larger than twice the diameter of the cell, the cell cannot sufficiently cover the fine pore, concentration of the lines of electric force occurs and plural cells tend to be drawn by dielectrophoretic force, and thereby the probability that at least two cells enter each fine pore increases. When cell fusion is aimed to be carried out while fixing at least two cells in each fine pore, the diameter of the fine pore may be larger than that of the cell to be fixed in the fine pore. However, when cell fusion is aimed to be carried out while fixing a single cell in each fine pore, it is preferable that the diameter of a maximum circle inscribed in a planar shape of the fine pore be no less than equal to but less than twice as large as that of the cell to be fixed therein and the depth of the fine pore be no larger than the diameter of the cell to be fixed therein.

In order to fix a single cell in each fine pore, it is preferable that the distance between the adjacent fine pores be neither extremely narrow nor large. When the distance between the adjacent fine pores is extremely narrow, the probability that plural cells are fixed in each fine pore increases, as a result of which the probability of generating a fine pore in which no cells are fixed increases. While, when the distance between the adjacent fine pores is extremely large, some of the cells remain between the fine pores, and so the probability of generating fine pores in which no cells are fixed increases. Accordingly, it is specifically preferable that the distance between the adjacent fine pores be no less than 0.5 times but less than 6 times, more preferably approximately within a range from equal to twice as large as the diameter of the cell to be fixed therein.

When the period of the plateau in which a predetermined voltage having a level other than 0 is maintained for a predetermined time is no longer than the time constant calculated by multiplying a cellular capacitance by a resistance of a cell suspension containing the cells, Condenser A (29) shown in FIG. 17 is not sufficiently charged, and so the current continues flowing to Condenser A (29) and then to Fine pore A' (17), as a result of which the concentration of the lines of electric force occurs. Accordingly, Cell A" (10") tends to be drawn to Fine pore A' (17) in which Cell A' (10') enters, and thus the probability that at least two cells are fixed in each fine pore increases.

Figure 2:
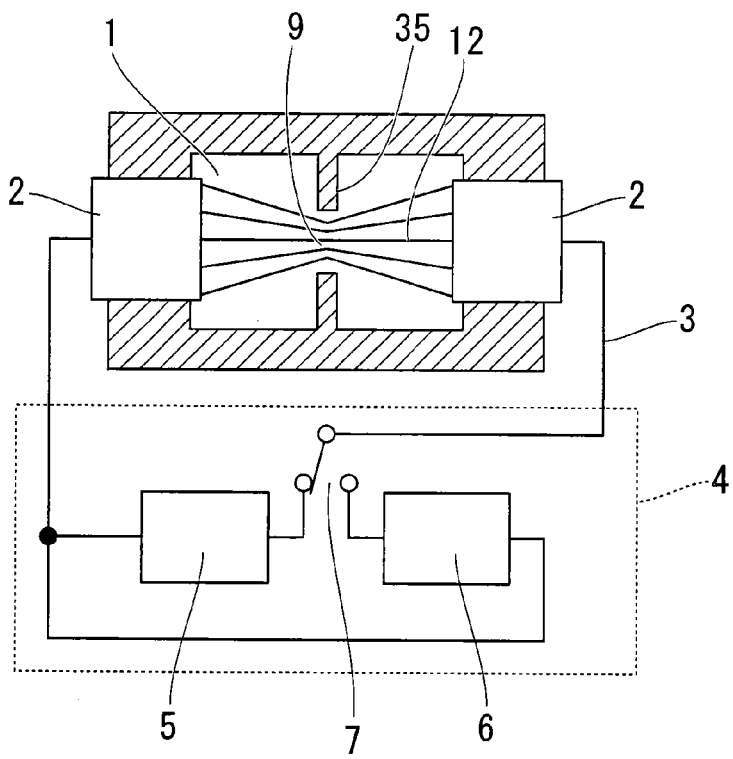
FIG. 2 is a first drawing illustrating the performance of the cell fusion chamber described in Patent Document 1.
Figure 3:
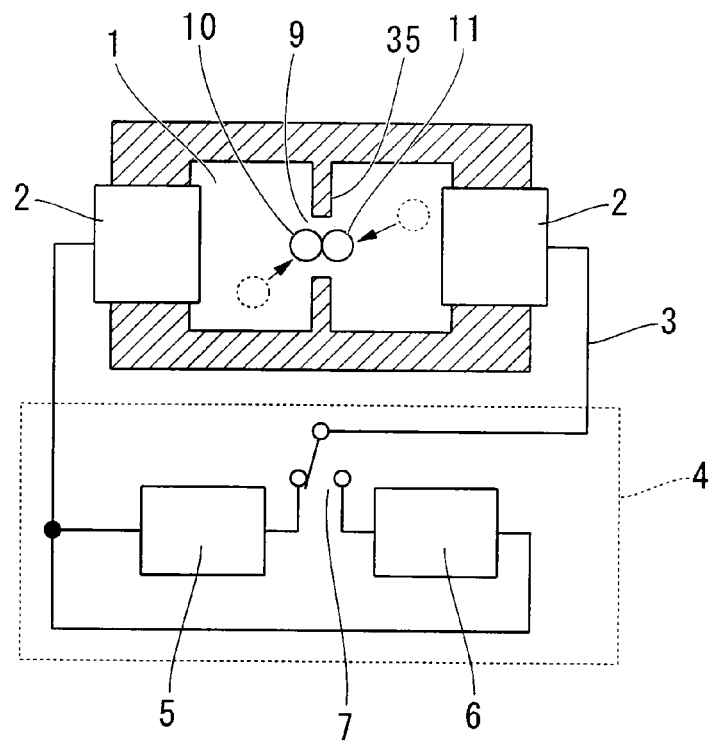
FIG. 3 is a second drawing illustrating the performance of the cell fusion chamber described in Patent Document 1.
Figure 4:
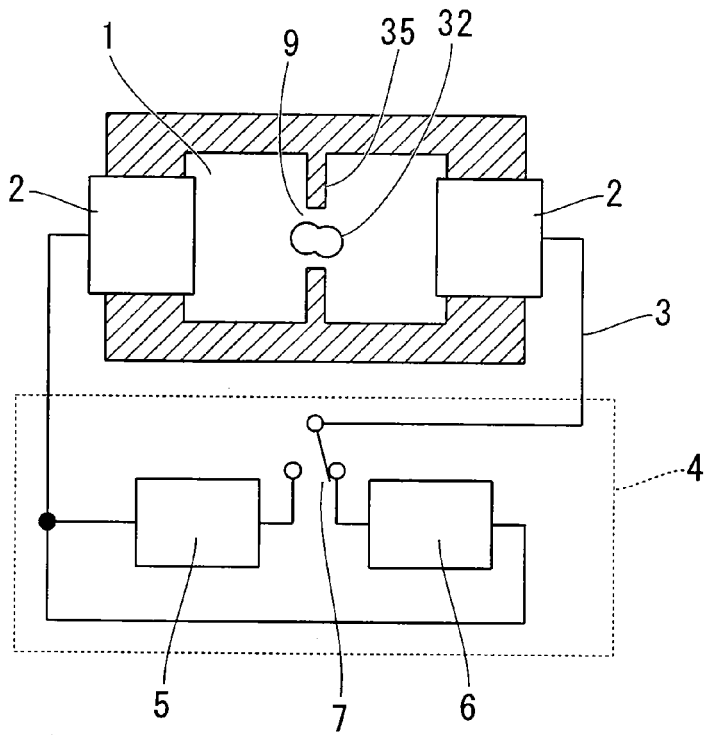
FIG. 4 is a third drawing illustrating the performance of the cell fusion chamber described in Patent Document 1.
Figure 22:
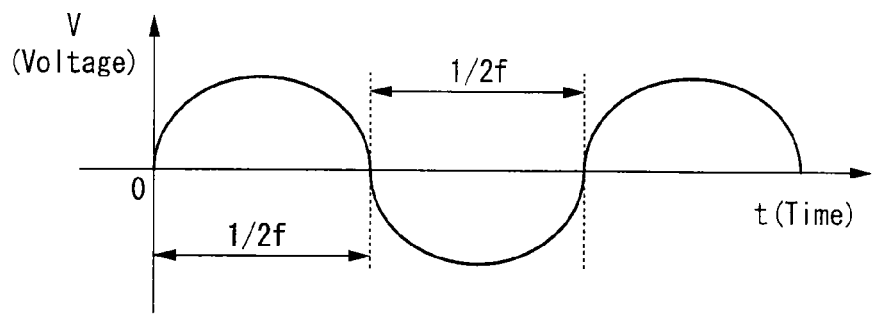
FIG. 22 is a drawing showing a waveform of a sine-wave alternating voltage with frequency f [Hz].
Figure 23:
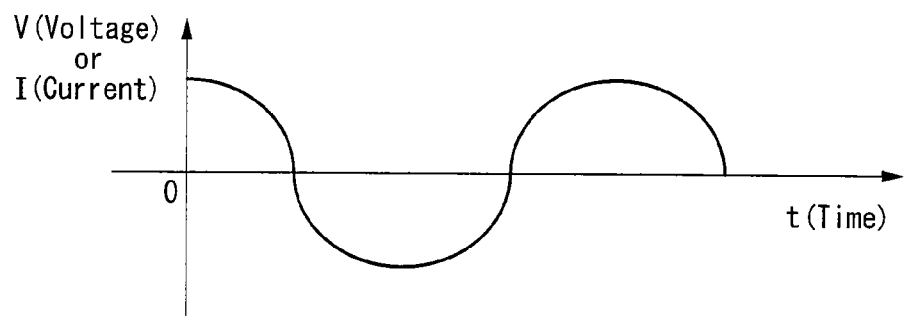
FIG. 23 is a drawing showing a current waveform of a Condenser A shown in FIG. 17, the waveform being output when a sine-wave alternating voltage with frequency f [Hz] as shown in FIG. 22 is applied between electrodes.

Next, when an alternating voltage having a sine waveform with a frequency f [Hz] is applied as shown in FIG. 22, the lines of electric force are concentrated to the fine pore, and so the dielectrophoretic force acts on the cells in the same manner, and the cells are drawn to the fine pore by the dielectrophoretic force, as shown in FIG. 2 to FIG. 3. Thus, Cell A' (10') covers Fine pore A' (17). The portion of Fine pore A' (17) covered by Cell A' (10') becomes electrically equivalent to Condenser A (29) as shown in FIG. 17. The voltage waveform and the current waveform in Condenser A (29) measured when the voltage having the waveform as shown in FIG. 22 is applied are shown in FIG. 23. When the alternating voltage having a sine wave waveform is applied, the voltage waveform and the current waveform in Condenser A (29) have a phase of the sine-wave merely shifted by 90° without changing the waveform of the sine-wave, as shown in FIG. 23. Accordingly, the current continues flowing to Fine pore A' (17) in which Cell A' (10') enters, and the concentration of lines of electric force occurs. Therefore, Cell A" (10") may be drawn to Fine pore A' (17) in which Cell A' (10') enters, and the probability of at least two cells being fixed in each fine pore increases. Accordingly, when an alternating voltage continuously changing with a waveform such as a sine-wave or chopping wave is applied, it tends to be difficult to fix a single cell in each fine pore, because some fine pores tend to include plural cells fixed therein, while some fine pores tend to include no cells fixed therein. When the applied voltage is a direct current, ions contained in the cell suspension cause electrical reaction on the surfaces of the electrodes, the electrical reaction generates heat, and thereby the cells are set into thermal motion, as a result of which it tends to be difficult to control the cell handling by the dielectrophoretic force and to draw the cells to the fine pore.

As described above, the cell fusion device according to the present invention enables a single cell to be reliably fixed in each fine pore plurally disposed in an array state on the insulator, when the waveform of the alternating voltage applied from the alternating-current power supply to the electrodes is the waveform periodically repeating charge and discharge of the cells, more specifically the waveform having per half cycle thereof at least one plateau in which a predetermined voltage at a level other than 0 is maintained for a predetermined time, for example, a rectangular wave waveform, a trapezoidal wave waveform, or a waveform combining these waves, more preferably a period of the plateau being no less than the time constant calculated by multiplying a cellular capacitance by a resistance of the cell suspension, or alternatively the diameter of a maximum circle inscribed in a planar shape of the fine pore penetrating through the insulator is no less than equal to but less than twice as large as the diameter of the cell to be fixed in the fine pore, and the depth of the fine pore is no larger than, preferably approximately the same as the diameter of the cell, the distance between the adjacent fine pores plurally disposed is no less than 0.5 times but less than 6 times as large as the diameter of the cell to be fixed therein, and more preferably, the plural fine pores are formed in an array state.

According to the cell fusion method, a first cell is fixed in a first fine pore, and then a second cell is fixed onto the fixed first cell. The second cell is affected by the dielectrophoretic force, the gravity, and the electrostatic force of the first cell, and so the second cell makes contact with the first cell. However, the current scarcely flows to the fine pore covered by the first cell because of the above-mentioned reasons, and so the generation of the lines of electric force is suppressed. Accordingly, the dielectrophoretic force acting on the second cell weakens, and so the probability of bringing the second cell into contact with the first cell fixed in the fine pore one by one tends to decrease. However, the probability of contact between the first cell and the second cell can be enhanced by increasing the content of the second cell with respect to that of the first cell and introducing an excess of the second cell into the cell fusion region.

Next, the cell fusion method according to the present invention will be explained in more detail using drawings.

The cell fusion method is a method for fusing cells using the above-mentioned cell fusion device. According to the cell fusion method, the first cell is introduced into the cell fusion region, and then an alternating voltage is applied to fix the first cell into the fine pore. After fixing the first cell in the fine pore, the second cell is introduced into the cell fusion region, and an alternating voltage is applied to bring the second cell into contact with the first cell at the fine pore, followed by applying a voltage pulsed direct current to fuse the first and second cells making contact. It is preferable that the alternating voltage has the above-mentioned waveform of alternating voltage.

Figure 24:
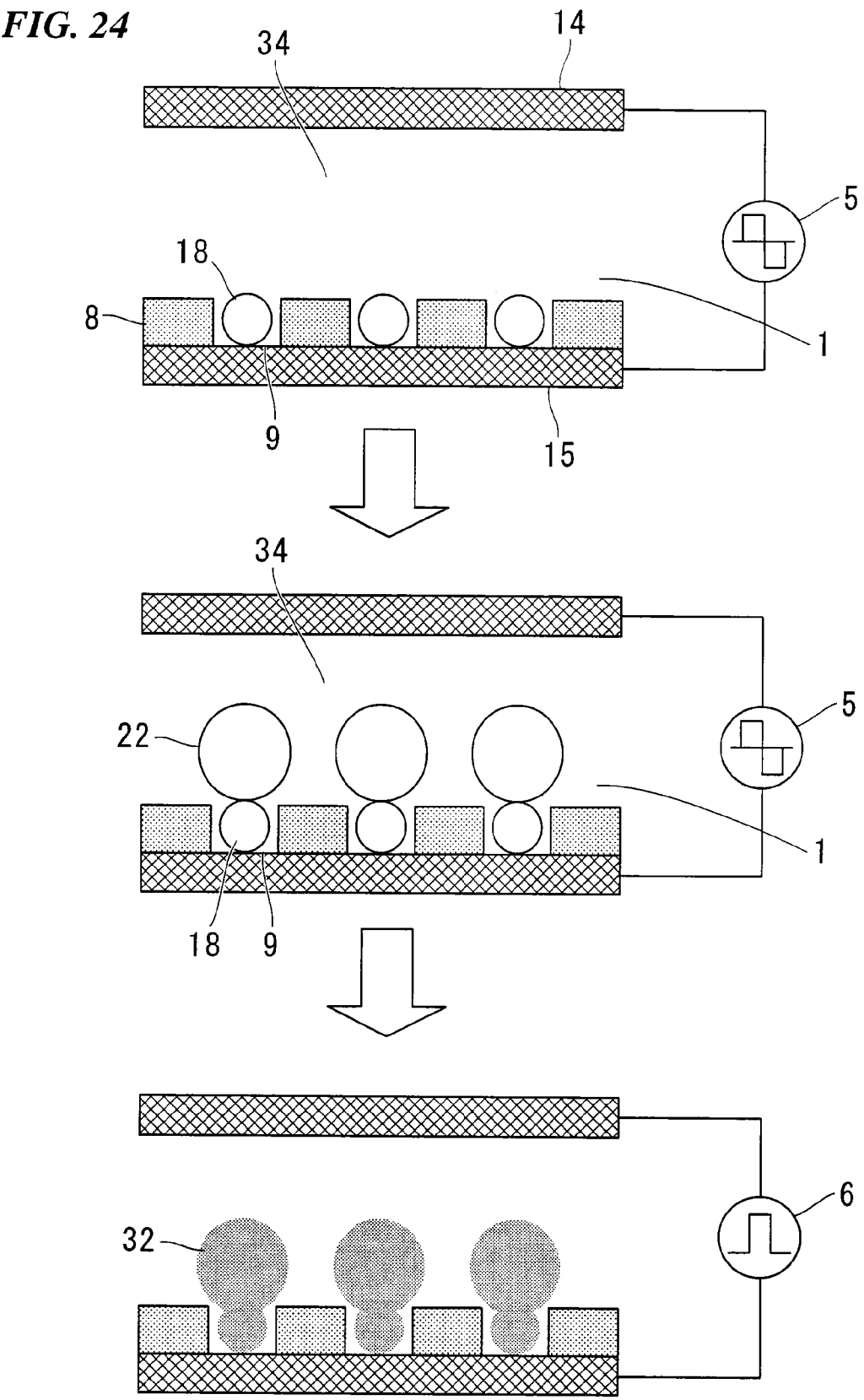
FIG. 24 is a drawing illustrating a first embodiment of a method for cell fusion according to the present invention.
Figure 25:
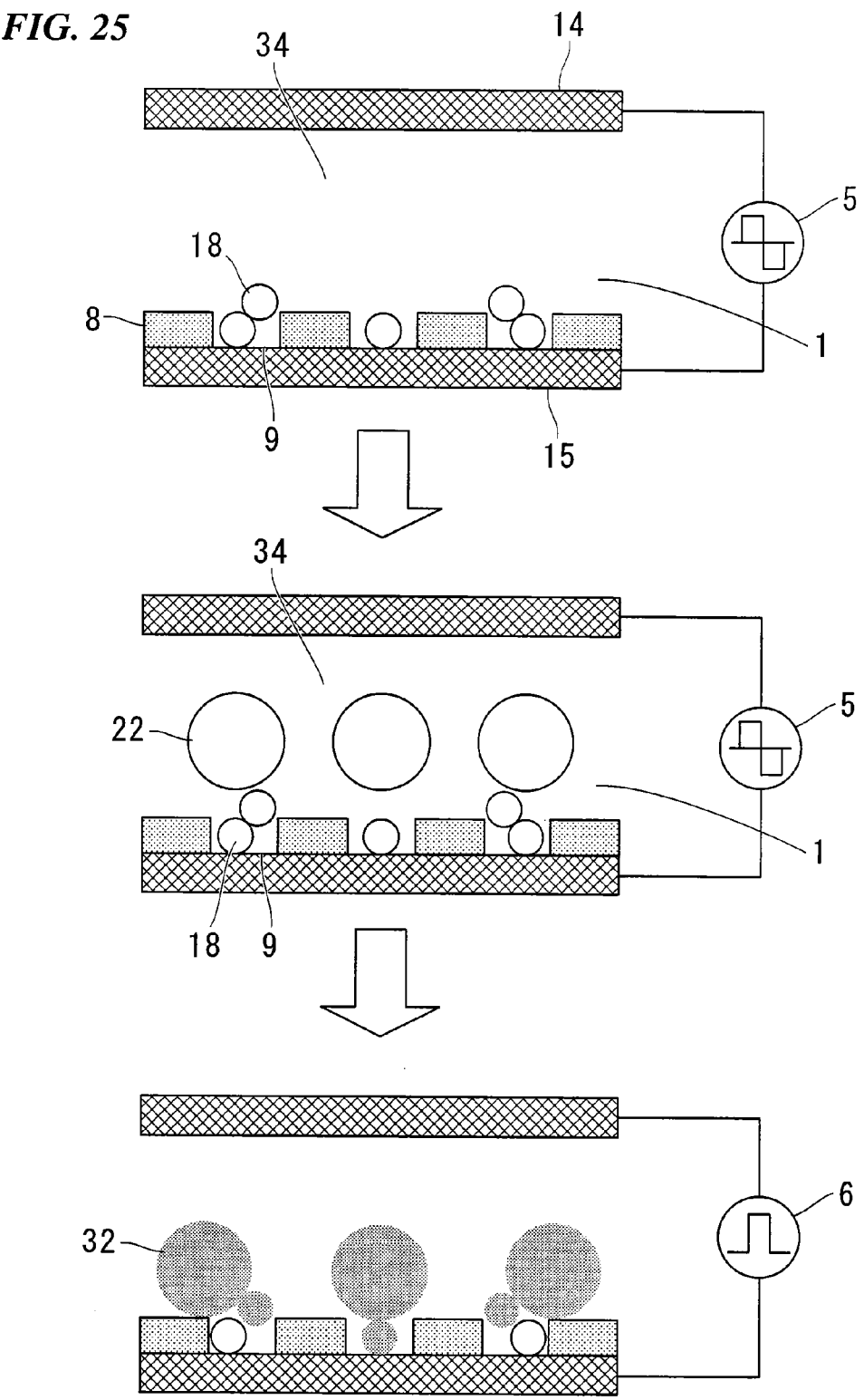
FIG. 25 is a drawing illustrating a second embodiment of a method for cell fusion according to the present invention.

FIG. 24 and FIG. 25 are schematic views showing embodiments of the cell fusion method according to the present invention. In these embodiments, the diameter of the first cell is smaller than that of the second cell. In the cell fusion method according to the present invention, it is preferable that the diameter of the first cell be smaller than that of the second cell, and more preferably the diameter of the fine pore be no larger than that of the second cell and no smaller than that of the first cell. According to this, the first cell can be reliably fixed in the fine pore, the second cell introduced after the first cell is reliably fixed in the fine pore can be effectively brought into contact with the first cell, and thereby pairs of the first and second cells making contact can be effectively fused. However, the diameter of the first cell may be substantially equal to or larger than the second cell. In the cell fusion method according to the present invention, although it is preferable that the first cell and the second cell be fused at a farthest position of the fine pore from the bottom of the fine pore, the first cell and the second cell may be fused substantially inside the fine pore. It is apparent that changes and modifications may be arbitrarily made in these embodiments shown in FIG. 24 and FIG. 25 without departing from the scope of the present.

In FIG. 24, the diameter and depth of the fine pore (9) are approximately equal to the diameter of a first cell (18), and so the first cell just enters the fine pore (9). In FIG. 25, the diameter of the fine pore (9) is larger than that of the first cell (18), and the depth of the fine pore (9) is approximately equal to the diameter of the first cell (18).

The embodiment of the cell fusion method shown in FIG. 24 is the best. First of all, a cell suspension (34) containing the first cell (18) having a small diameter is introduced into the cell fusion region (1), and an alternating voltage having the above-mentioned waveform is applied to fix each first cell (18) in each fine pore (9). In this case, the first cell (18) is induced to the fine pore (9) mainly affected by the dielectrophoretic force, gravity, and electrostatic force from the electrodes. The diameter and the depth of the fine pore (9) are approximately equal to that of the first cell (18), and so the first cell (18) just enters the fine pore (9). According to this, electrostatic force is generated on the bottom surface of the fine pore (9) and the surface of the electrode, and so the first cell (18) is reliably fixed in the fine pore (9). Although the first cell (18) number is not particularly limited, it is preferably equal to that of the fine pore (9) in order to effectively use the first cell (18).

Next, a cell suspension containing a second cell (22) having a large diameter is introduced into the cell fusion region (1). At this time, since the first cell (18) is fixed by the electrostatic force generated between the first cell (18) and the electrode (15), and the first cell (18) is surrounded by walls of the fine pore (9), the first cell (18) scarcely separates from the fine pore (9) when the suspension containing the second cell is introduced into the cell fusion region (1). The introduced second cell (22) is brought into contact with the first cell (18) from the top thereof and fixed to the first cell (18) by applying the alternating voltage having the above-mentioned waveform. In this case, although the dielectrophoretic force generated in the fine pore (9) acts on the second cell (22), the gravity and the electrostatic force generated from the first cell (18) mainly act on the second cell (22), and induce the second cell (22) to the first cell (18) fixed in the fine pore (9). Although the second cell (22) number to be introduced is not particularly limited, it is preferably approximately equal to that of the fine pore (9) in order to effectively use the second cell (22). However, the number of second cells (22) may be over that of the fine pore (9) in order to enhance the probability of contact between the first cell (18) and the second cell (22).

Next, an electronic power supply is switched to the direct current pulsed power supply (6) from the alternating-current power supply (5) for changing the connection with the electrodes, and a voltage pulsed direct current is applied to the electrodes, thereby pairs of the first cell (18) and the second cell (22) are effectively fused.

Figure 26:
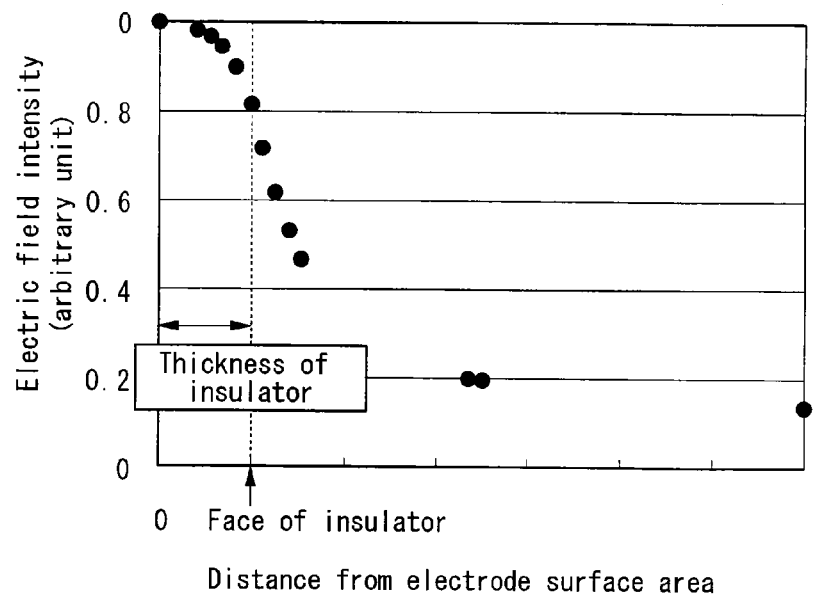
FIG. 26 is a drawing showing the intensity of an electrical field near fine pores.

Since the lines of electric force are concentrated to the fine pore, the electrical field intensity onto the electrode (15) inside the fine pore (9) is the highest in the electrical field intensity outside (near) the fine pore and the electrical field intensity gradually decreases from the insulator (8) (insulating film face) to the upper electrode (14), as shown in FIG. 26. FIG. 26 shows changes in the electrical field intensity generated when the insulator with an arbitrary film thickness has a fine pore having an arbitrary diameter and depth and is disposed on one of the electrodes and an arbitrary voltage is applied between the electrodes, the electrical field intensity being calculated using a finite element method. In FIG. 26, the longitudinal axis shows levels of the electrical field intensity normalized by the maximum electrical field intensity, and the horizontal axis shows the distance from the electrode on which the insulator is disposed. The electrical field intensity at the electrode on which the insulator is disposed is shown at the origin of the horizontal axis. The electrical field intensity at a position separated from the insulator-side electrode with a distance of the same length as that of the thickness of the insulator (the farthest position of the fine pore from the bottom of the fine pore) is shown by a dot crossing a dotted line, and the electrical field intensity inside the fine pore is shown between the origin of the horizontal axis and the dotted line. In this calculation, the electrical field intensity does not depend on the raw material and film thickness of the insulator, or the diameter and depth of the fine pore. As shown in FIG. 26, the electrical field intensity on the surface of the electrode inside the fine pore is higher by approximately 20% than that of the farthest position of the fine pore from the insulator-side electrode.

In general electrical cell fusion methods, electrical conductance of cellular membranes instantly decreases by applying a voltage pulsed direct current, and then reversible disruption and reconstitution of the cellular membranes composed of a lipid bilayer are caused, and thus cells are fused. In general, the smaller the diameter of the cell, the higher the voltage pulsed direct current required for causing reversible disruption of the cellular membranes. When the first cell having a smaller diameter is firstly fixed in the fine pore, and the second cell having a larger diameter is fixed on the fixed first cell, and then a voltage pulsed direct current is applied between the electrodes, the electrical field intensity inside the fine pore is higher than that outside the fine pore as shown in FIG. 26, and so the voltage substantially applied to the first cell fixed inside the fine pore is higher than that applied to the second cell fixed outside the fine pore, that is, the voltage substantially applied to the first cell having a smaller diameter is higher by approximately 20% than that applied to the second cell having a larger diameter. According to this, it is possible to compensate for the difference in voltage level required for causing reversible disruption of membranes of cells having different diameters.

As described above, even when the second cell is excessively introduced into the cell fusion region by making the concentration of the second cell higher than that of the first cell so as to increase the probability of contact between the first cell and the second cell, the electrical field intensity in the fine pore is the highest and the electrical field intensity weakens in accordance with the distance from the fine pore as shown in FIG. 26. Accordingly, by suitably adjusting the level of the voltage pulsed direct current, membranes of the first and second cells making contact are reversibly disrupted and fused. Thus, it is possible to selectively fuse only the first and second cells making contact at the fine pore.

According to the present invention, the following effects can be exhibited.

(1) By making the cell fusion chamber according to the present invention have the following components: the cell fusion region; a pair of the electrodes formed by a conductor and disposed opposite to each other in the cell fusion region; and the partition wall disposed between the pair of electrodes to divide the cell fusion region into two compartments, the partition wall having the fine pore penetrating through the partition wall in a direction of the pair of electrodes, and the fine pore having a diameter no larger than that of the cell having a larger diameter than the other cell and no smaller than that of the cell having a smaller diameter than the other cell, it becomes possible to make two types of the cells having different diameters contact with each other at the fine pore in the same direction of that of the lines of electric force, and so reliably fuse the cells. It is possible to take out the fused cells with ease by aspirating the fused cells from the side of the compartment into which the cell having a larger diameter is introduced, or pressurizing the cell suspension from the compartment into which the cell having a smaller diameter is introduced. Accordingly, it is possible to more reliably carry out an electrical cell fusion and to take out the fused cells rapidly.

(2) By disposing the insulator having the fine pore onto the cell fusion region-side electrode in the cell fusion device according to the present invention, it is possible to reliably fix the cell in the fine pore, and so to selectively and effectively fuse pairs of two cells.

(3) By making the diameter of a maximum circle inscribed in a planar shape of the fine pore of the cell fusion device according to the present invention be no less than equal to but less than twice as large as that of the cell to be fixed in the fine pore and the depth of the fine pore be no larger than the diameter of the fine pore to be fixed therein, it is possible to reliably fix the cell in the fine pore.

(4) By forming plural fine pores in an array state in the insulator of the cell fusion device according to the present invention, it is possible to fuse plural pairs of two cells at the same time, and thus cell fusion of plural pairs of two cells can be effectively carried out.

(5) By making the distance between the adjacent fine pores in the cell fusion device according to the present invention be no less than 0.5 times but less than 6 times as large as the diameter of the cell to be fixed in the fine pore, the probability of fixing a single cell in each fine pore can be enhanced, and so the probability of contact between two cells at each fine pore can be enhanced.

(6) By controlling the waveform of the alternating voltage applied from the alternating-current power supply to the electrodes, it is possible to reliably fix a single cell in each fine pore.

(7) Since the cell fusion method according to the present invention is a cell fusion method using the above-mentioned cell fusion device, in which the first cell is introduced into the cell fusion region and fixed in the fine pore by applying an alternating voltage to the electrodes, the second cell is then introduced into the cell fusion region, brought into contact with the first cell at the fine pore by applying the alternating voltage to the electrodes, and then fused with the first cell by applying a voltage pulsed direct current, the alternating voltage preferably being an alternating voltage having the waveform, and the first and second cells making contact being preferably fused near the farthest position of the fine pore from the insulator-side electrode, it is possible to selectively fuse pairs of two cells near the fine pore, and thus cell fusion of pairs of two cells can be effectively carried out.

(8) By making the diameter of the first cell smaller than that of the second cell in the cell fusion method according to the present invention, it is possible to compensate for the difference in voltage level decreasing with distance from the bottom surface of the fine pore, because the voltage level required for causing reversible disruption of cellular membrane increases in inverse proportion to the diameter of the cell to be fused.

EXAMPLES

In the following, the present invention will be explained in more detail with reference to Examples and Comparative Examples. It should be apparent that the present invention is not limited to these examples and it is capable of arbitrary modification without departing from the scope of the present invention.

Example 1

Figure 36:
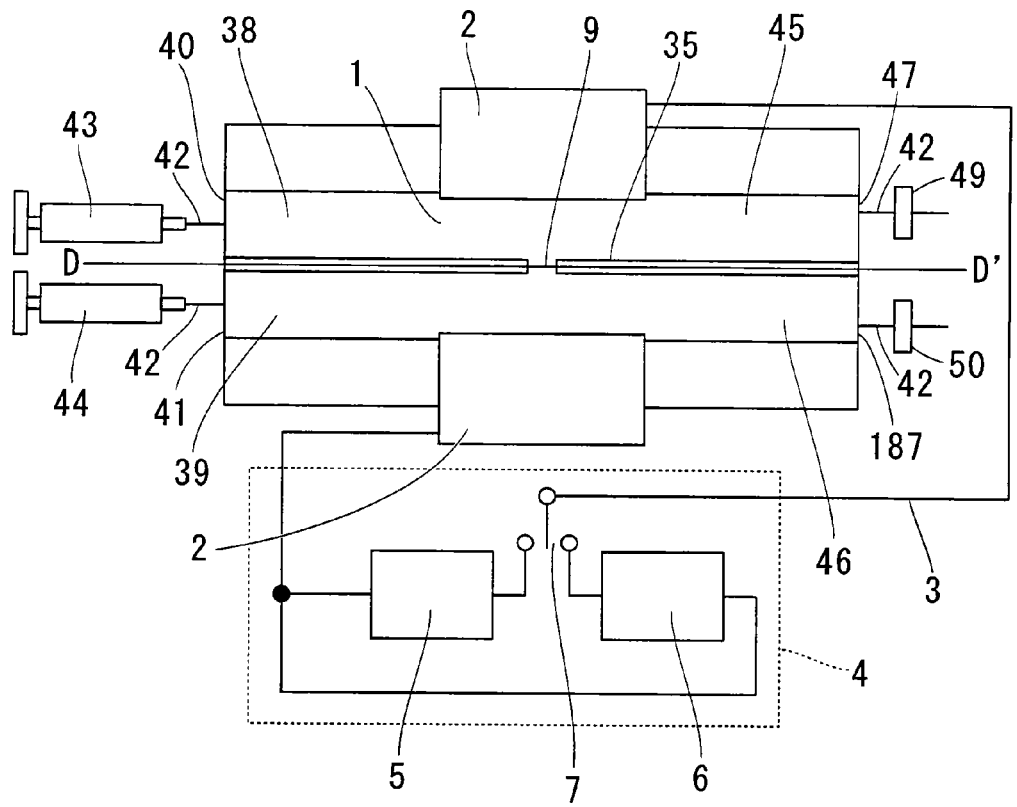
FIG. 36 is a schematic diagram of a cell fusion chamber used in Example 1.
Figure 37:
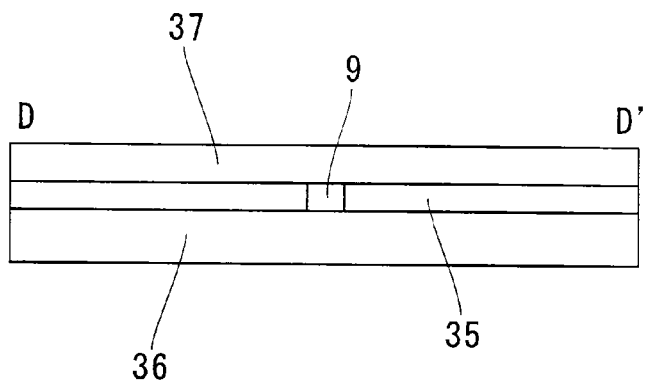
FIG. 37 is a cross-sectional drawing of DD' portion of the cell fusion chamber shown in FIG. 36.

A cell fusion chamber used in Example 1 is schematically shown in FIG. 36. Also, FIG. 37 is a cross-sectional drawing of the DD' region shown in FIG. 36. A substrate (36) was made of a transparent silicone resin. In the substrate (36), a dent portion was formed to form the cell fusion region (1). In the cell fusion region (1), a partition wall (35) was disposed so as to divide the cell fusion region (1) into two compartments, and the fine pore (9) was formed in the partition wall (35). At both sides of the cell fusion region (1), the electrodes (2) made of a conductor were disposed.

As shown in FIG. 37, the cell fusion chamber was formed by adhering while pressurizing a cover body (37) onto the substrate (36). The cover body (37) was the same dimension as that of the substrate (36) and was made using the transparent silicone resin as a raw material similar to that of the substrate (36). The reason the substrate (36) and the cover body (37) were made using the transparent raw material was that the transparent material enabled the state of cell fusion carried out in the cell fusion chamber to be observed using a microscope.

As shown in FIG. 36, each channel connected with the cell fusion region (1) and formed a passage through which a cell suspension containing cells was transferred. Cell introducing channel A (38) connected with Pump A (43) through Cell inlet A (40) and a tube (42) and so enabled Cell A (10) to be introduced into one of the compartments of the cell fusion region (1) divided in two by the partition wall (35). Also, Cell introducing channel B (39) connected Pump B (44) through Cell inlet B (41) and the tube (42) and so enabled Cell B (11) to be introduced into the other compartment of the cell fusion region. As Pump A (43) and Pump B (44), syringe pumps which could flow a suspension by pressurizing were used. Cell exhaust channel A (45) connected with Valve A (49) through Cell outlet A (47) and the tube (42). Also, Cell exhaust channel B (46) connected with Valve B (50) through Cell outlet B (48) and the tube (42). Valve A (49) and Valve B (50) were respectively opened when Cell A (10) and Cell B (11) were introduced using Pump A (43) and Pump B (44). When two cells reached near the fine pore (9), Pump A (43) and Pump B (44) were stopped and Valve A (49) and Valve B (50) were closed so as to fix the cells near the fine pore (9). To the electrodes (2), the electronic power supply (4) as shown in FIG. 1 was connected through the conductor (3).

As the raw material of the substrate (36) and the cover body (37) of the cell fusion chamber shown in FIG. 36, polymer materials such as natural rubber, epoxy, or the like may be used in addition to silicone resins. Since chemically inactive materials are preferably used, the raw material is not limited to polymer materials, and glass, ceramic materials such as carbonaceous ceramics, alumina, apatite, zirconia, or the like may also be used as the raw material. The dent portion formed in the substrate (36) may be formed using various process methods suitable for the raw material to be used, such as machining process, wet etching, dry etching, molding, or the like.

Figure 12:
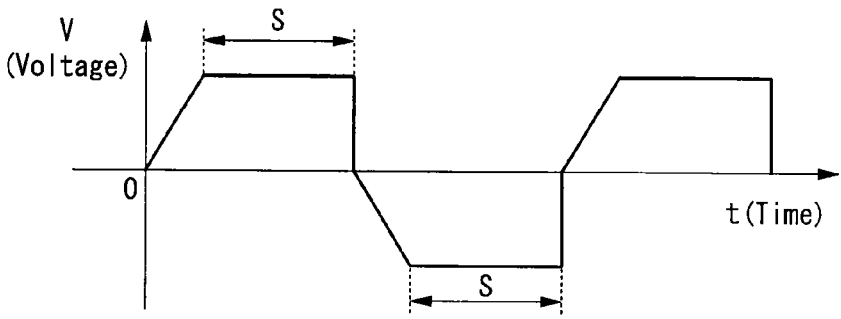
FIG. 12 is a drawing showing a combination waveform of a rectangular wave and a trapezoidal wave as another example of a waveform of an alternating voltage used in the present invention.
Figure 38:
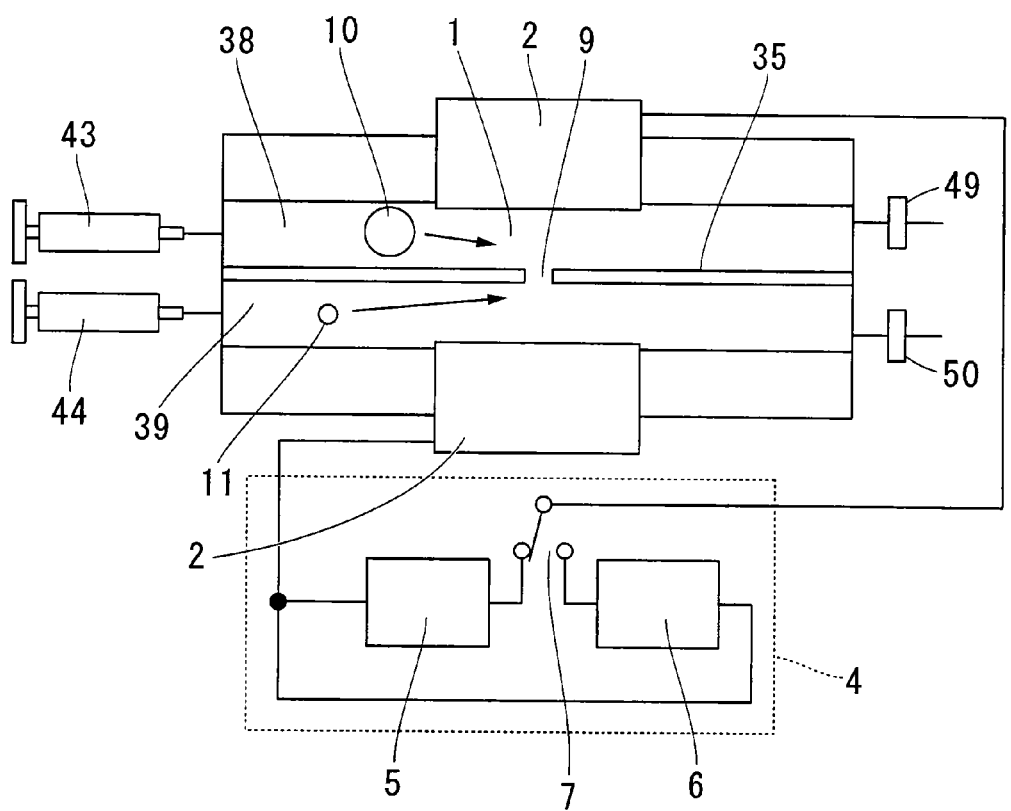
FIG. 38 is a first drawing illustrating the performance of the cell fusion chamber used in Example 1.
Figure 39:
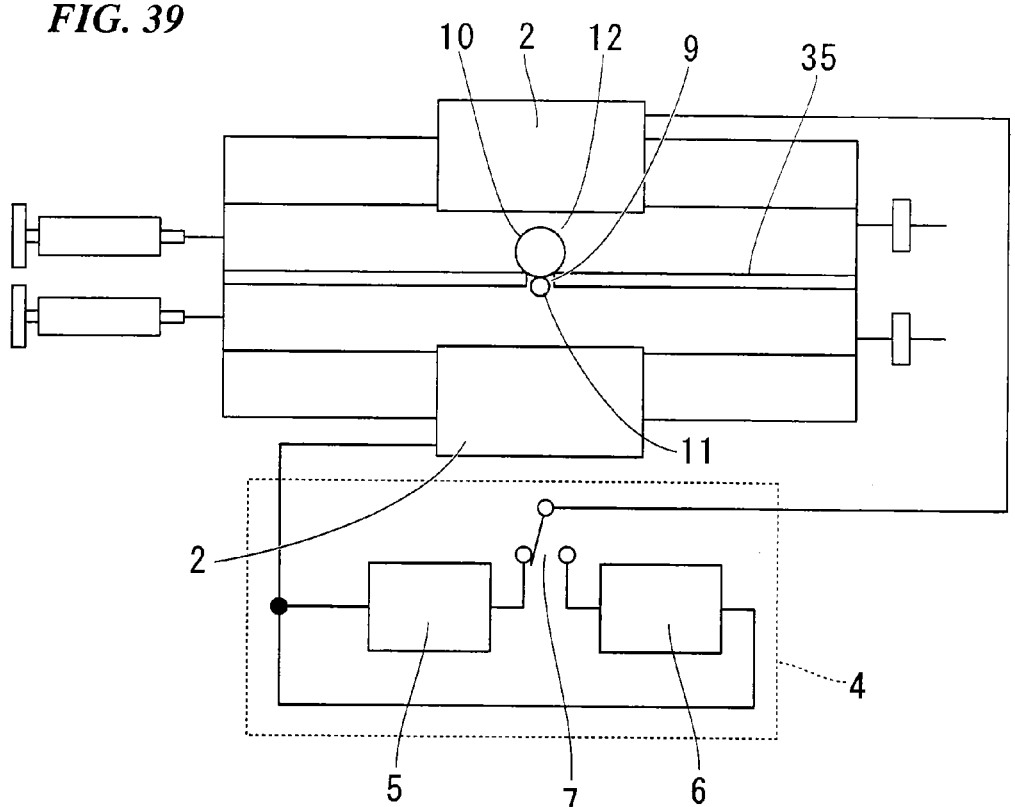
FIG. 39 is a second drawing illustrating the performance of the cell fusion chamber used in Example 1.

Next, the process for cell fusion using the cell fusion chamber as shown in FIG. 36 and FIG. 37 will be explained using FIG. 38 to FIG. 41. The manipulation for cell fusion was carried out while observing the manipulation from the upper surface of the cell fusion chamber using a microscope. In FIG. 38, Valve A (49) and Valve B (50) were opened, and the suspension containing Cell A (10) was sent using Pump A (43) and the suspension containing Cell B (11) was sent using Pump B (44). At this time, the switch (7) of the electronic power supply (4) connected an alternating-current power supply (5) with the electrodes (2). Cell A (10) and Cell B (11) contained in the sent suspensions were respectively introduced into the cell fusion region (1) through Cell introducing channel A (38) and Cell introducing channel B (39). When Cell A (10) and Cell B (11) reached near the fine pore (9), Valve A (49) and Valve B (50) were closed to prevent the cells from being widely transferred. When the cells approached the fine pore (9), the cells were affected by the dielectrophoresis due to lines of electric force concentrating at the fine pore (9), and so the cells were trapped near the center of fine pore (9) as shown in FIG. 12. Since the diameter of Cell A (10) was larger than that of the fine pore (9), Cell A was trapped so as to cover the fine pore (9), while since the diameter of Cell B (11) was smaller than that of the fine pore (9), Cell B (11) passed through the fine pore (9) and reliably contacted with Cell A (10) in directions of the lines of electric force.

Figure 40:
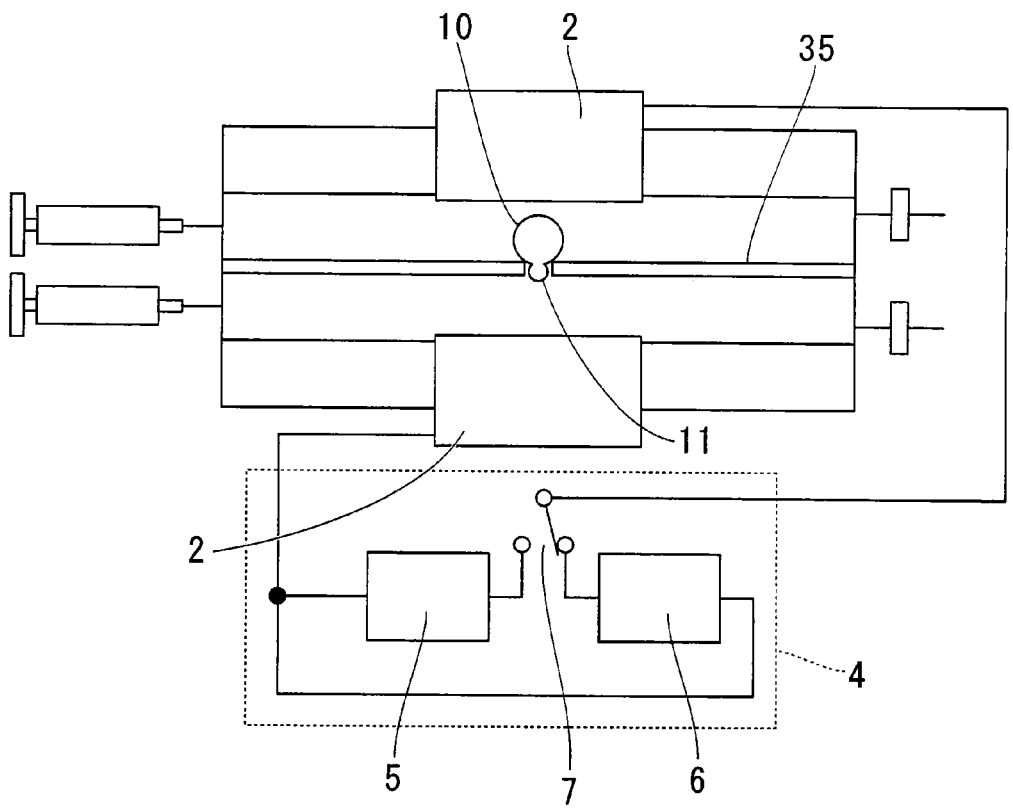
FIG. 40 is a third drawing illustrating the performance of the cell fusion chamber used in Example 1.
Figure 41:
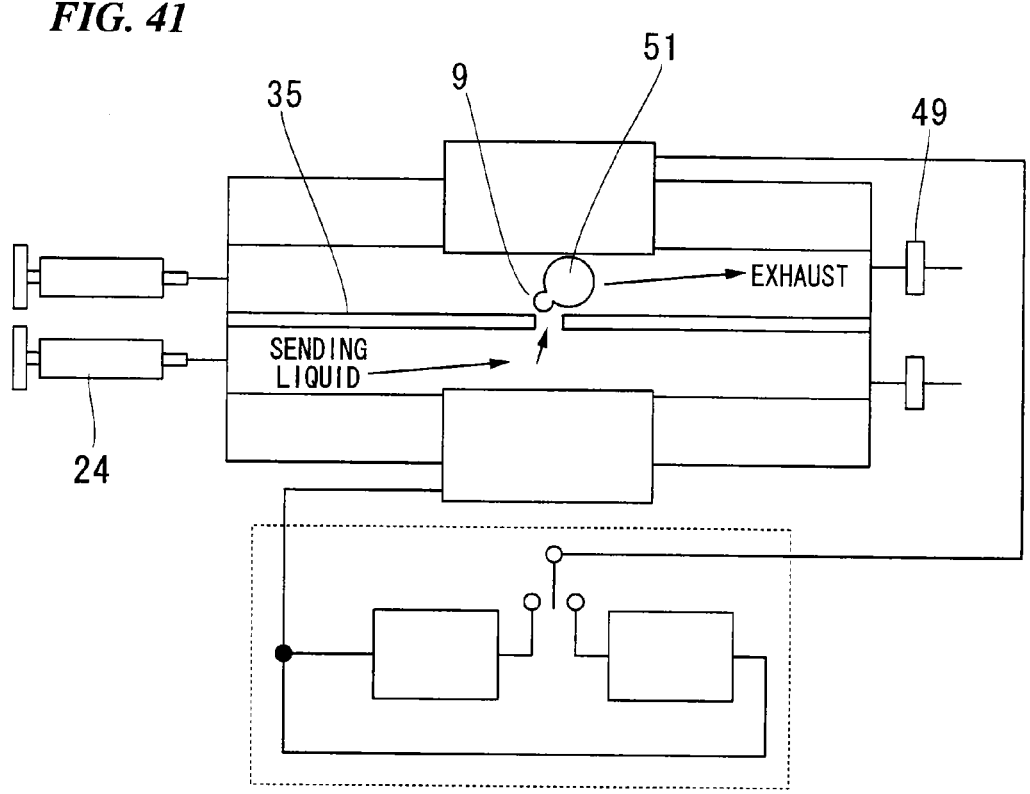
FIG. 41 is a fourth drawing illustrating the performance of the cell fusion chamber used in Example 1.

Next, the switch (7) of the electronic power supply (4) connected the direct current pulsed power supply (6) to the electrodes (2). As shown in FIG. 40, cellular membranes of Cell A (10) and Cell B (11) were reversibly disrupted due to an output pulsed voltage at the contact point between Cell A (10) and Cell B (11), and thus cell fusion occurred. Next, as shown in FIG. 41, Valve A (49) used to introduce Cell A (10) was opened and the suspension was sent from pump B (24), thereby the fused cell (51) could be easily taken out.

Example 2

A cell fusion device used in Example 2 is schematically shown in FIG. 7. The cell fusion device was mainly composed of the cell fusion container (13) and the electronic power supply (4). As shown in FIG. 7, the cell fusion container (13) had a structure in which the spacer (16) was disposed between the upper electrode (14) and the lower electrode (15), and the insulator (8) having plural fine pores (9) formed in an array state was disposed between the spacer (16) and the lower electrode (15). In Example 2, an all-in-one unit formed by a general photolithography and etching technique so that the insulator (8) having plural fine pores (9) formed in an array state was integrated into the lower electrode (15) was used as described below.

Figure 27:
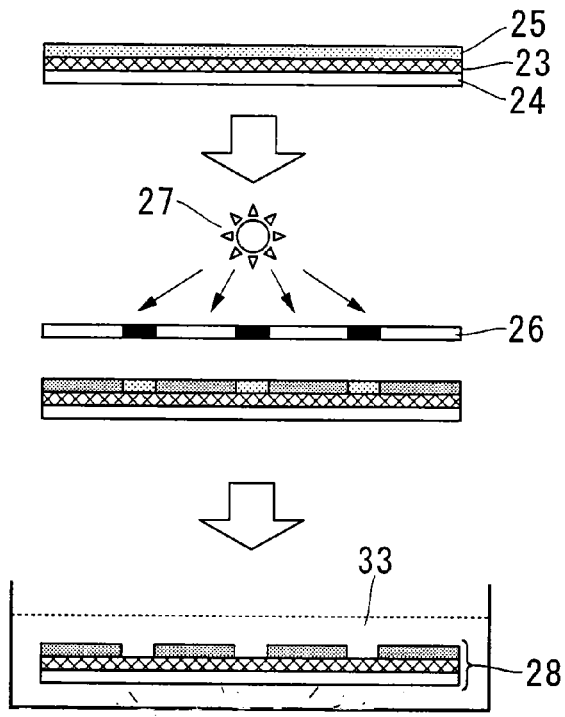
FIG. 27 is a schematic view illustrating a general photolithography and etching technique.

As the upper electrode (14) and the lower electrode (15), one in which ITO (Indium Tin Oxide) was coated with a film thickness of 150 nm onto a Pyrex (registered trademark) substrate with a dimension of 70 mm in length, 40 mm in width, and 1 mm in thickness was used. The spacer (16) was formed from a silicone sheet with a dimension of 40 mm in length, 40 mm in width, and 1.5 mm thickness, and its center portion with a dimension of 20 mm in length and 20 mm in width was hollowed out to form a through-hole. Also, the inlet (19) through which a cell suspension was to be introduced and the outlet (20) through which the cell suspension was to be exhausted were disposed in the spacer (16), as shown in FIG. 7. The insulator (8) having the plural fine pores (9) was formed to be integrated into the lower electrode (15) by a photolithography and etching technique as shown in FIG. 27.

Next, the photolithography and etching technique will be explained in more detail. First of all, a resist (25) was coated with a film thickness of 2.5 μm using a spin coater onto an ITO film formed by coating ITO (23) onto a Pyrex (registered trademark) glass (24). After the film was air dried for 45 minutes, prebaking (80° C., 15 minutes) was carried out using a hot plate. As the resist, a xylene-based negative resist was used. Next, the resist (25) was exposed (27) using an UV exposure device with an exposure photomask (26) having a dimension of 30 mm in length and 30 mm in breadth. In the exposure photomask (26), patterns of fine pore having a diameter φ of 7 μm were arranged in longitudinal and horizontal lines so that each line included 1000 patterns with longitudinal and horizontal intervals of 30 μm. Then, development was carried out using a developing agent (33). Exposure time and developing time were determined so that the depth of the formed fine pore became 2.5 μm, equal to the film thickness of the resist (25), and thus ITO (23) appeared at the bottom of the fine pore. After development, postbaking (115° C., 30 minutes) was carried out using the hot plate so as to harden the resist (25), and thus the all-in-one unit (28) was formed.

Then, the upper electrode (14), the spacer (16), and the all-in-one unit (28) including the lower electrode (15) and the insulator (8) having fine pores (9) were multiply laminated and then adhered while pressurizing as shown in FIG. 8. FIG. 8 is a cross-sectional drawing of BB' region of the cell fusion container shown in FIG. 7. Since the surface of the silicone sheet had stickiness, each component made close contact by pressure bonding, and so the cell suspension could be held inside the cell fusion container without leaking. Since the dimension of the through-hole of the spacer (16) was 20 mm in length and 20 mm in breadth, the number of fine pores communicating with this through-hole was approximately four hundred thousand.

The electronic power supply (4) which enabled application of a voltage between the electrodes was composed of a signal generator (manufactured by NF Corporation, WF 1966) as the alternating-current power supply, an electro cell fusion power supply (manufactured by NEPA GENE, LF 101) as the direct current pulsed power supply, the conductor (3) connecting the alternating-current power supply and the direct current pulsed power supply with the cell fusion container (13), and the switch changing the connection with the electrodes between the alternating-current power supply and the direct current pulsed power supply.

As cells, a mouse spleen cell (having a diameter φ of 5 μm) and a mouse myeloma cell (having a diameter φ of 10 μm) were used. Both cells were each suspended into a mannitol aqueous solution having a concentration of 300 mM to prepare each cell suspension having a density of $0.7 \times 10^6$ cell/ml. To both of the prepared cell suspensions, 0.1 mM calcium chloride and 0.1 mM magnesium chloride were added so as to promote regeneration of membranes of fused cells.

600 μL of the cell suspension containing the mouse spleen cell (containing approximately four hundred thousand cells) was introduced from the inlet (19) of the spacer (16) using a syringe, and an alternating voltage having a rectangular waveform, a voltage level of 10 Vpp, and a frequency of 3 MHz was applied between the electrodes from the alternating-current power supply. When the alternating voltage was applied for an extremely short time, approximately a few seconds, each mouse spleen cell could be fixed in each fine pore formed plurally in an array state, and thus plural cells could be arranged in an array state. At this time, the probability that a single mouse spleen cell entered in each fine pore was 35%.

Then, 600 μL of the cell suspension containing the mouse myeloma cell (containing approximately four hundred thousand cells) was introduced from the inlet (19) of the spacer (16) using a syringe, while applying the alternating voltage having a rectangular waveform, a voltage level of 10 Vpp, and a frequency of 3 MHz between the electrodes from the alternating-current power supply. When the alternating voltage was applied for an extremely short time, approximately a few seconds, each mouse myeloma cell could be fixed at each fine pore formed plurally in an array state, and thus a plural cells could be arranged in an array state. At this time, the probability that one myeloma cell was fixed at each fine pore was 55%. Since no mouse spleen cells removed from the fine pore by introducing the mouse myeloma cells were observed, the probability that pairs of the mouse spleen cell and the mouse myeloma cell made contact at each fine pore was presumed to be approximately 20% (calculated by multiplying 35% by 55%).

Next, the electronic power supply was switched to the direct current pulsed power supply (manufactured by NEPA GENE, LF 101), and a voltage pulsed direct current having a voltage level of 80 V and a pulse width of 30 μs was applied between the electrodes to fuse the cells. After leaving the cells still for 10 minutes without change, a liquid component of the cell suspension in the cell fusion container was replaced with a HAT medium (containing the following components: H (hypoxanthine); A (aminopterine); and T (thymidine)) and the fused cells were cultured in the HAT medium. The HAT medium is a medium which enables the fused cells to selectively proliferate. The HAT medium containing the cells was placed in a $CO_2$ incubator to culture the cells for 6 days, and the number of fused cells was counted. As a result, 40 fused cells were observed, which revealed that the fusion probability was 1/10000 with respect to all of four hundred thousand mouse spleen cells. This probability was 5 times higher than that exhibited by a conventional electrical cell fusion method in Comparative Example 1 described below, the probability of Comparative Example 1 being 0.2/10000. Thus, effective cell fusion of pairs of two cells could be observed.

Comparative Example 1

In Comparative Example 1, electrical cell fusion was conventionally carried out. As electrodes used for electrical cell fusion, gold wire electrodes with a 1-mm gap (manufactured by NEPA GENE, MS gold wire electrode) were used, and an electronic cell fusion power supply (manufactured by NEPA GENE, LF 101) was connected to the electrodes.

As cells, a mouse spleen cell (having a diameter $\phi$ of 5 μm) and a mouse myeloma cell (having a diameter y of 10 μm) were used. The mouse spleen cell and the mouse myeloma cell were mixed in a ratio of 4:1, and suspended in a mannitol aqueous solution having a concentration of 300 mM. The cell suspension was adjusted to have a density of $1.7 \times 10^7$ cells/mL. In order to promote regeneration of cellular membranes, 0.1 mM calcium chloride and 0.1 mM magnesium chloride were added to the cell suspension.

40 μL of the cell suspension (containing approximately six hundred thousand cells of the mouse spleen cell and approximately one hundred fifty thousand cells of the mouse myeloma cell) was introduced between the electrodes, and an alternating voltage having a sine-wave, a voltage level of 20 Vpp, and a frequency of 3 MHz was applied between the electrodes from the electronic cell fusion power supply. After confirming the cells were arranged in a pearl chain state, a voltage pulsed direct current having a voltage level of 200 V and a pulse width of 30 us was applied to fuse the cells. After leaving still for 10 minutes, a liquid component of the cell suspension was replaced with the HAT medium. The HAT medium containing the cells was placed in a $CO_2$ incubator to culture the cells for 6 days, and the number of fused cells was counted. As a result, 12 fused cells were observed, which reveals that the fusion probability was 0.2/10000 with respect to all of six hundred thousand mouse spleen cells.

Comparative Example 2

Figure 28:
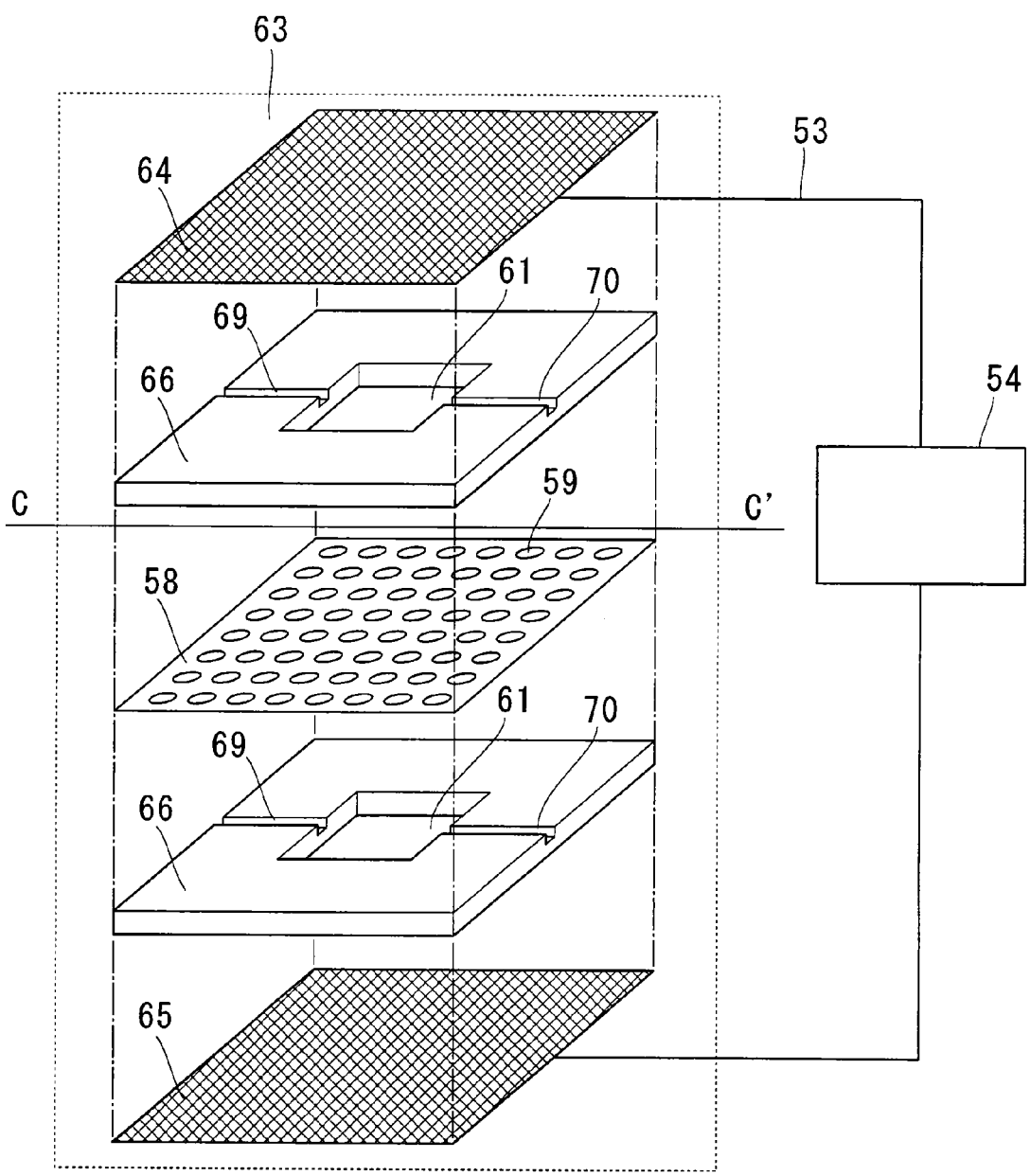
FIG. 28 is a schematic view illustrating a cell fusion device used in Comparative Example 2.

A cell fusion device used in Comparative Example 2 is schematically shown in FIG. 28. The cell fusion device was mainly composed of a cell fusion container (63) and an electronic power supply (54). In the cell fusion container as shown in FIG. 28, two sheets of spacer (66) were disposed between an upper electrode (64) and a lower electrode (65). Between the two sheets of spacer (66), an insulator (58) having plural fine pores (59) formed in an array state was disposed. As the upper electrode (64) and the lower electrode (65), one in which ITO was coated with a film thickness of 150 nm onto a Pyrex (registered trademark) substrate with a dimension of 70 mm in length, 40 mm in breadth, and 1 mm in thickness was used.

The spacer (66) was formed from a silicone sheet with a dimension of 40 mm in length, 40 mm in breadth, and 1 mm in thickness, and its centre portion with a dimension of 20 mm in length and 40 mm in breadth was hollowed out to form a through-hole. Also, an inlet (69) through which a cell suspension was introduced and an outlet (70) through which the cell suspension was exhausted were formed in each spacer (66), as shown in FIG. 28. The insulator (58) having plural fine pores (59) was made from a polyimide film with a dimension of 40 mm in length, 40 mm in breadth, and 25 μm in thickness using a photolithography and etching technique so that fine pores having a diameter $\phi$ of 20 μm were formed in an array state in the centre portion with a dimension of 30 mm in length and 30 mm in breadth. The longitudinal and horizontal distance between the adjacent fine pores was 50 μm, and the longitudinal and horizontal number of fine pores was 300 cells.

Figure 29:
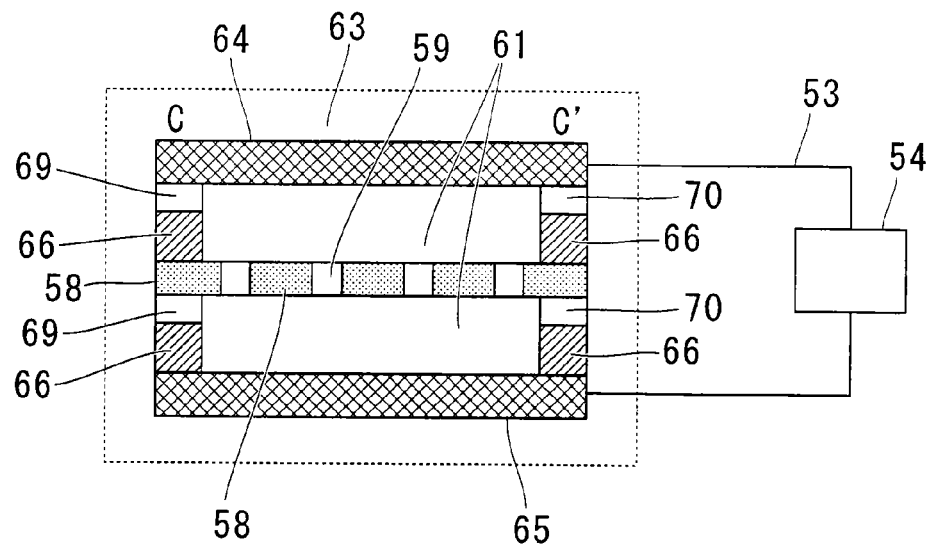
FIG. 29 is a cross-sectional drawing of CC' portion of a cell fusion container of the device shown in FIG. 28.
Figure 30:
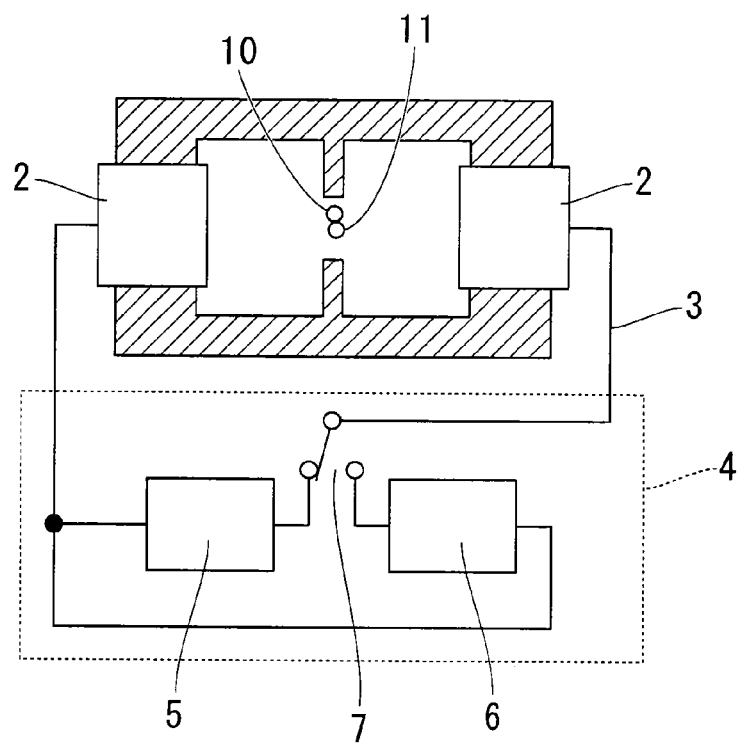
FIG. 30 is a schematic diagram showing a conventional example in which the diameter of a fine pore is larger than those of two cells.
Figure 31:
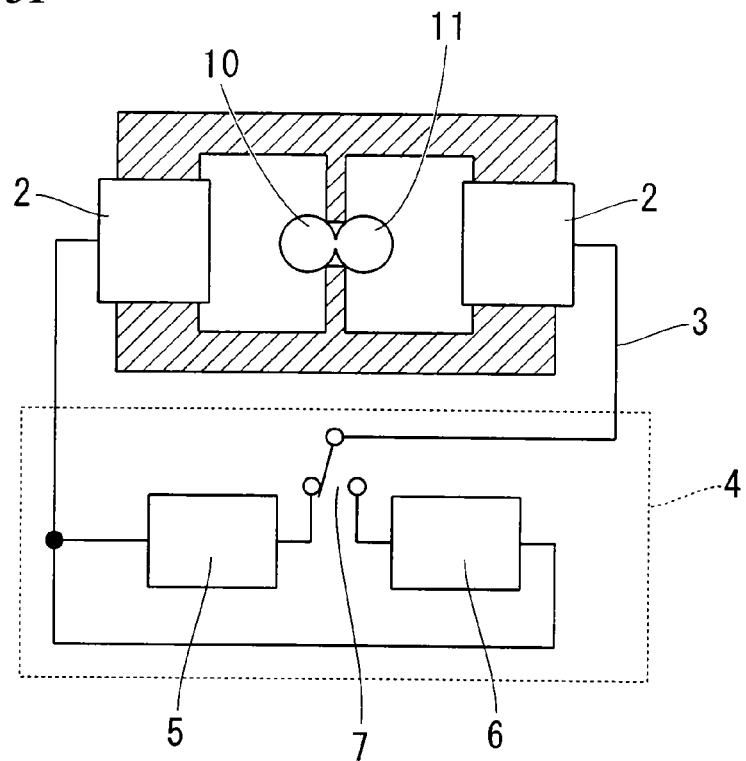
FIG. 31 is a schematic diagram showing a conventional example in which the diameter of a fine pore is smaller than those of two cells.

Then, the upper electrode (64), the spacers (66), the insulator (58) having fine pores (59), and the lower electrode (65) were multiply laminated and then adhered while pressurizing as shown in FIG. 29. FIG. 29 is a cross-sectional drawing of CC' region of the cell fusion container shown in FIG. 28. Since the surface of the silicone sheet had stickiness, each component closely made contact by pressure bonding, and so the cell suspension could be held inside the cell fusion container without leaking. Since the dimension of the through-hole of the spacer (66) was 20 mm in length and 20 mm in breadth, the number of fine pores communicating with this through-hole was approximately four hundred thousand.

An electronic power supply which enabled application of a voltage between the electrodes was composed of a signal generator (manufactured by NF Corporation, WF 1966) as the alternating-current power supply, an electro cell fusion power supply (manufactured by NEPA GENE, LF 101) as the direct current pulsed power supply, a conductor (53) connecting an alternating-current power supply and a direct current pulsed power supply with the electrodes, and the switch changing the connection with the electrodes between the alternating-current power supply or the direct current pulsed power supply.

A mouse spleen cell (having a diameter $\phi$ of 5 μm) and a mouse myeloma cell (having a diameter $\phi$ of 10 μm) were used. Both cells were respectively suspended into a mannitol aqueous solution having a concentration of 300 mM to prepare each cell suspension having a density of $0.7 \times 10^6$ cell/ml. To both of the prepared cell suspensions, 0.1 mM calcium chloride and 0.1 mM magnesium chloride were added so as to promote regeneration of membranes of fused cells.

600 μL of the cell suspension containing the mouse spleen cell (containing approximately four hundred thousand cells) was introduced from the inlet (69) of the spacer (66) using a syringe, and an alternating voltage having a rectangular waveform, a voltage level of 15 Vpp, and a frequency of 3 MHz was applied between the electrodes from the signal generator. When the alternating voltage was applied for an extremely short time, approximately a few seconds, the mouse spleen cells could be fixed in the fine pores formed in an array state. However, there were some fine pores in which plural mouse spleen cells were fixed and some fine pores in which no mouse spleen cells were fixed, and thus approximately no fine pores in which one mouse spleen cell was fixed in each fine pore could be observed.

Then, 600 μL of the cell suspension containing the mouse myeloma cell (containing approximately four hundred thousand cells) was introduced from the inlet (69) of the spacer (66) using a syringe, while applying the alternating voltage having a rectangular waveform, a voltage level of 15 Vpp, and a frequency of 3 MHz between the electrodes from the alternating-current power supply. As a result, almost all the mouse spleen cells previously fixed in the fine pores were removed from the fine pores, and so the mouse spleen cell and the mouse myeloma cell could not be fused at the fine pores.

What is claimed is:

1. A method for fixing a cell, comprising:
    introducing a cell into a container comprising: a pair of electrodes formed by a conductor and disposed opposite to each other; a tabular spacer disposed between the pair of electrodes; and a tabular insulator disposed between the spacer and one of the electrodes and having pores penetrating through the insulator in a direction of the pair of electrodes; and
    applying an alternating voltage to the electrodes with an electronic power supply to fix a single cell in each of the pores, wherein
    each of the pores has a shape that traps a single cell,
    the alternating voltage has a waveform periodically repeating charge and discharge of cells,
    the alternating voltage has a waveform including per half cycle thereof at least one plateau in which a predetermined voltage at a level other than 0 is maintained for a predetermined time (S[s]),
    the predetermined time is no shorter than a time constant ($\tau$[s]) that is calculated by multiplying a cellular capacitance (C[F]) by a resistance (R[$\omega$]) of a cell suspension,
    the predetermined time satisfies the following relationship: $S \geq \tau (= C \cdot R)$,
    the applying the alternating voltage includes applying a rectangular waveform with a frequency (f[Hz]) satisfying the following relationship: $\tau < \frac{1}{2} \cdot f$, such that when a first cell is charged, a current does not flow, and the current flows to the first cell in a pulse state with flow durations of the time constant $\tau$ between which the current does not flow,
    when the rectangular waveform is applied, lines of electric force are concentrated at a first pore to draw the first cell into the first pore by dielectrophoretic force,
    when the first cell is drawn into the pore, a portion of the first pore covered with the first cell becomes electrically equivalent to the insulator and the lines of electric force are no longer concentrated at the first pore to decrease a probability that the first pore draws in another cell, and lines of electric force are concentrated in a second pore to draw a second cell into the second pore by dielectrophoretic force, and
    cells are repeatedly drawn into vacant pores by the applying the alternating voltage.

2. The method according to claim 1, wherein the insulator is disposed on a side-surface of one of the electrodes.

3. The method according to claim 1, wherein a diameter of a maximum circle inscribed in a planar shape of the first pore is no less than equal to but less than twice as large as that of the first cell to be fixed in the first pore, which is configured to surely fix the first cell.

4. The method according to claim 1, wherein the insulator has the plural pores in a face thereof, each of the pores being formed evenly spaced apart from adjacent pores, so that an electrical field is approximately evenly created in all of the pores by the alternating voltage.

5. The method according to claim 1, wherein the insulator has the plural pores in a face thereof formed in an array state, so that an electrical field is approximately evenly created in all of the pores by the alternating voltage.

6. The method according to claim 1, wherein the insulator has the plural pores in a face thereof, and a distance between adjacent pores of the pores is no less than 0.5 times but less than 6 times as large as a diameter of a cell to be fixed in the respective pores, to enhance a probability of fixing a single cell in each of the pores.

7. The method according to claim 1, wherein the spacer has a through-hole.

8. The method according to claim 1, further comprising:
    introducing cells into the container through an introducing channel of the spacer.

* * * * *